(12) United States Patent
Dekel et al.

(10) Patent No.: US 9,808,488 B2
(45) Date of Patent: Nov. 7, 2017

(54) ISOLATED POPULATIONS OF RENAL STEM CELLS AND METHODS OF ISOLATING AND USING SAME

(71) Applicant: Tel HaShomer Medical Research Infrastructure and Services Ltd., Ramat-Gan (IL)

(72) Inventors: Benjamin Dekel, Tel-Aviv (IL); Orit Harari-Steinberg, RaAnana (IL)

(73) Assignee: Tel HaShomer Medical Research Infrastructure and Services Ltd., Ramat-Gan (IL)

( * ) Notice: Subject to any disclaimer, the term of this patent is extended or adjusted under 35 U.S.C. 154(b) by 546 days.

(21) Appl. No.: 14/479,385

(22) Filed: Sep. 8, 2014

(65) Prior Publication Data
US 2015/0139963 A1 May 21, 2015

Related U.S. Application Data

(62) Division of application No. 13/203,282, filed as application No. PCT/IL2010/000158 on Feb. 25, 2010, now Pat. No. 8,828,722.

(60) Provisional application No. 61/202,425, filed on Feb. 26, 2009, provisional application No. 61/202,426, filed on Feb. 26, 2009.

(51) Int. Cl.
| | |
|---|---|
| A61K 35/12 | (2015.01) |
| A61K 35/22 | (2015.01) |
| C12N 5/071 | (2010.01) |
| C12N 5/074 | (2010.01) |
| C12N 15/85 | (2006.01) |

(52) U.S. Cl.
CPC ............ A61K 35/22 (2013.01); C12N 5/0686 (2013.01); C12N 5/0687 (2013.01); C12N 5/0696 (2013.01); C12N 15/85 (2013.01); C12N 2500/90 (2013.01); C12N 2501/06 (2013.01); C12N 2501/065 (2013.01); C12N 2501/415 (2013.01); C12N 2506/25 (2013.01)

(58) Field of Classification Search
CPC .......................... A61K 2121/00; C12N 5/0687
See application file for complete search history.

(56) References Cited

U.S. PATENT DOCUMENTS

| | | |
|---|---|---|
| 2002/0102241 A1 | 8/2002 | Arnaout et al. |
| 2002/0119565 A1 | 8/2002 | Clarke et al. |
| 2004/0014209 A1 | 1/2004 | Lassar et al. |
| 2005/0026023 A1 | 2/2005 | Hirai et al. |
| 2007/0031966 A1 | 2/2007 | Dressler et al. |
| 2007/0065942 A1 | 3/2007 | Wandinger-Ness et al. |
| 2010/0097794 A1 | 4/2010 | Teng et al. |
| 2011/0311494 A1 | 12/2011 | Benjamin et al. |
| 2011/0311495 A1 | 12/2011 | Dekel |
| 2013/0059325 A1 | 3/2013 | Dekel |
| 2014/0011280 A1 | 1/2014 | Dekel et al. |

FOREIGN PATENT DOCUMENTS

| | | |
|---|---|---|
| WO | WO 2005/021738 | 3/2005 |
| WO | WO 2010/097793 | 9/2010 |

OTHER PUBLICATIONS

Communication Pursuant to Article 94(3) EPC Dated Dec. 19, 2014 From the European Patent Office Re. Application No. 11728406.7.
Communication Pursuant to Article 94(3) EPC Dated Jan. 22, 2014 From the European Patent Office Re. Application No. 11728406.7.
Communication Pursuant to Article 94(3) EPC Dated Jan. 28, 2013 From the European Patent Office Re. Application 10710685.8.
Communication Pursuant to Article 94(3) EPC Dated Jan. 28, 2013 From the European Patent Office Re. Application No. 10712582.5.
Communication Relating to the Results of the Partial International Search Dated Jun. 28, 2010 From the International Searching Authority Re. Application No. PCT/IL2010/000158.
European Search Report and the European Search Opinion Dated Jan. 24, 2013 From the European Patent Office Re. Application No. 11188963.0.
International Preliminary Report on Patentability Dated Sep. 9, 2011 From the International Bureau of WIPO Authority Re. Application No. PCT/IL2010/000158.
International Preliminary Report on Patentability Dated Sep. 9, 2011 From the International Bureau of WIPO Re. Application No. PCT/IL2010/000159.
International Preliminary Report on Patentability Dated Nov. 22, 2012 From the International Bureau of WIPO Re. Application No. PCT/IL2011/000376.
International Search Report and the Written Opinion Dated Oct. 11, 2010 From the International Searching Authority Re. Application No. PCT/IL2010/000158.
International Search Report and the Written Opinion Dated Jun. 18, 2010 From the International Searching Authority Re. Application No. PCT/IL2010/000159.
International Search Report and the Written Opinion Dated Sep. 26, 2011 From the International Searching Authority Re. Application No. PCT/IL2011/000376.
Office Action Dated Oct. 7, 2013 From the Israel Patent Office Re. Application No. 214837 and Its Translation Into English.
Office Action Dated Oct. 9, 2013 From the Israel Patent Office Re. Application No. 216043 and Its Translation Into English.
Office Action Dated Jan. 22, 2015 From the Israel Patent Office Re. Application No. 214837.
Office Action Dated Apr. 23, 2014 From the Israel Patent Office Re. Application No. 214783 and Its Translation Into English.
Office Action Dated Oct. 27, 2013 From the Israel Patent Office Re. Application No. 214783 and Its Translation Into English.
Official Action Dated Apr. 2, 2014 From the US Patent and Trademark Office Re. U.S. Appl. No. 13/697,531.
Official Action Dated Aug. 8, 2013 From the US Patent and Trademark Office Re. U.S. Appl. No. 13/203,282.
Official Action Dated Sep. 12, 2014 From the US Patent and Trademark Office Re. U.S. Appl. No. 13/697,531.

(Continued)

Primary Examiner — Lynn Y Fan

(57) ABSTRACT

Isolated populations of fetal renal stem cells and progenitor cells are provided. Also provided are methods of generating and using these isolated populations of cells.

9 Claims, 25 Drawing Sheets
(17 of 25 Drawing Sheet(s) Filed in Color)

(56) References Cited

OTHER PUBLICATIONS

Official Action Dated May 16, 2013 From the US Patent and Trademark Office Re. U.S. Appl. No. 13/203,277.
Official Action Dated Mar. 23, 2015 From the US Patent and Trademark Office Re. U.S. Appl. No. 13/697,531.
Restriction Official Action Dated Apr. 11, 2013 From the US Patent and Trademark Office Re. U.S. Appl. No. 13/203,282.
Restriction Official Action Dated Feb. 25, 2013 From the US Patent and Trademark Office Re. U.S. Appl. No. 13/203,277.
Restriction Official Action Dated Dec. 31, 2013 From the US Patent and Trademark Office Re. U.S. Appl. No. 13/697,531.
Translation Dated Feb. 9, 2015 of Office Action Dated Jan. 22, 2015 From the Israel Patent Office Re. Application No. 214837.
Alison et al. "Attributes of Adult Stem Cells", The Journal of Pathology, XP002602081, 217(2): 144-160, Jan. 2009. p. 149.
Araki et al. "Chromatin-Modifying Agents Permit Human Hematopoietic Stem Cells to Undergo Multiple Cell Divisions While Retaining Their Repopulating Potential", Blood, XP002583271, 109(8): 3570-3578, Apr. 15, 2007. p. 3570-3571.
Atala et al. "Applications of Tissue Engineering in the Genitourinary Tract", Expert Review of Medical Devices, 2(1): 119-126, Jan. 2005.
Balzar et al. "The Biology of the 17-1A Antigen (Ep-CAM)", The Journal of Molecular Medicine, 77: 699-712, 1999.
Boyle et al. "Fate Mapping Using Cited1-CreERT2 Mice Demonstrates That the Cap Mesenchyme Contains Self-Renewing Progenitor Cells and Gives Rise Exclusively to Nephronic Epithelia", Developmental Biology, 313: 234-245, 2008.
Brodbeck et al. "Genetic Determination of Nephrogenesis: The Pax/Eya/Six Gene Network", Pediatric and Nephrology, 19: 249-255, 2004.
Bussolati et al. "Isolation of Renal Progenitor Cells From Adult Human Kidney", American Journal of Pathology, XP002454238, 166(2): 545-555, Feb. 1, 2005.
Buzhor et al. "Kidney Spheroids Recapitulate Tubular Organoids Leading to Enhanced Tubulogenic Potency of Human Kidney-Derived Cells", Tissue Engineering Part A, XP55006582, 17(17-18): 2305-2319, Sep. 1, 2011.
Chang et al. "Contact Insensitivity of a Subpopulation of Normal Human Fetal Kidney Epithelial Cells and of Human Carcinoma Cell Lines1" Cancer Research, 47: 1634-1645, 1987.
Cirulli et al. "E-Cadherin NCAM, and EpCAM Expression in Human Fetal Pancreata", Transplantation Proceedings, 27(6): 3335, Dec. 1995.
Dekel et al. "Engraftment of Human Kidney Tissue in Rat Radiation Chimera: II. Human Fetal Kidneys Display Reduced Immunogenicity to Adoptively Transferred Human Peripheral Blood Mononuclear Cells and Exhibit Rapid Growth and Development", Transplantation, 64: 1550-1558, 1997. Abstract.
Dekel et al. "Human and Porcine Early Kidney Precursors as a New Source for Transplantion", Nature Medicine, XP002378906, 9(1): 53-60, Jan. 1, 2003.
Dekel et al. "Multiple Imprinted and Stemness Genes Provide a Link Between Normal and Tumor Progenitor Cells of the Developing Human Kidney", Cancer Research, XP002581965, 66(12): 6040-6049, Jun. 2006. p. 6040, Table 1.
Douville et al. "ALDH1 as a Functional Marker of Cancer Stem and Progenitor Cells", Stem Cells and Development, XP002602080, 18(1): 17-25, Jan. 2009.
Eccles et al. "Comparative In Situ Hybridization Analysis of PAX2, PAX8, and WT1 Gene Transcription in Human Fetal Kidney and Wilms' Tumors", American Journal of Pathology, 146(1): 40-45, Jan. 1995.
Garvin et al. "The In Vitro Growth, Heterotransplantation, and Immunohistochemical Characterization of the Bleastemal Component of Wilms' Tumor", American Journal of Pathology, 129(2): 353-363, Nov. 1987.
Gibson-D' Ambrosio et al. "Characteristics of long-term human epithelial cell cultures derived from normal human fetal kidney". In Vitro Cell Development and Biology, 23(4): 279-287, Apr. 1987. Abstract.
Harari-Steinberg et al. "Identification of Human Nephron Progenitors Capable of Generation of Kidney Structures and Functional Repair of Chronic Renal Disease", EMBO Molecular Medicine, 5(10): 1556-1568, Epub Sep. 2, 2013.
Hipp et al. "Sources of Stem Cells for Regenerative Medicine", Stem Cell Reviews, XP002583273, 4(1): 3-11, Apr. 2008. p. 7-8.
Hjelle et al. "Drug Metabolism in Isolated Proximal Tubule Cells: Aldehyde Dehydrogenase", Journal of Pharmacology and Experimental Therapeutics, XP009139110, 224(3): 699-706, Mar. 1, 1983.
Huangfu et al. "Induction of Pluripotent Stem Cells by Defined Factors Is Greatly Improved by Small-Molecule Compounds", Nature Biotechnology, XP002502536, 26(7): 795-797, Jul. 1, 2008. p. 795-796.
Imai et al. "Inhibition of Histone Deacetylase Activates Side Population Cells in Kidney and Partially Reverses Chronic Renal Injury", Stem Cells, XP002583269, 25(10): 2469-2475, 2007. p. 2469, 2473.
Jones et al. "Genomics of Renal Cell Cancer: The Biology Behind and the Therapy Ahead", Clinical Cancer Research, 13(2 Suppl.): 685s-692s, Jan. 15, 2007.
Kim et al. "Improvement of Kidney Failure With Fetal Kidney Precursor Cell Transplantation", Transplantation, 83: 1249-1258, 2007.
Kim et al. "Kidney Tissue Reconstruction by Fetal Kidney Cell Transplantation: Effect of Gestation Stage of Fetal Kidney Cells", Stem Cells, 25: 1393-1401, 2007.
Kobayashi et al. "Six2 Defines and Regulates a Multipotent Self-Renewing Nephron Progenitor Population Throughout Mammalian Kidney Development", Cell Stem Cell, 3: 169-181, 2008.
Kreidberg et al. "WT-1 Is Required for Early Kidney Development", Cell, 74: 679-691, 1993.
Kretzler et al. "Integrin-Linked Kinase as a Candidate Downstream Effector in Proteinuria", The FASEB Journal, 15(10): 1843-1845, Aug. 2001.
Liu et al. "Suspended Aggregates as an Immobilization Mode for High-Density Perfusion Culture of HEK 293 Cells in a Stirred Tank Bioreactor", Applied Microbiology and Biotechnology, XP019441688, 72(6): 1144-1151, Mar. 28, 2006. p. 1147, Table 1.
Lusis et al. "Isolation of Clonogenic, Long-Term Self Renewing Embryonic Renal Stem Cells", Stem Cell Research, XP027106369, 5(1): 23-29, Mar. 27, 2010. p. 27.
Maeshima et al. "Adult Kidney Tubular Cell Population Showing Phenotypic Plasticity, Tubulogenic Capacity, and Integration Capability Into Developing Kidney", Journal of the American Society of Nephrology, XP002471868, 17(1): 188-198, Jan. 1, 2006.
Markovic-Lipkovski et al. "Neural Cell Adhesion Molecule Expression on Renal Interstitial Cells", Nephrology Dialysis Transplantation, XP002581531, 22(6): 1558-1566, Jun. 2007. p. 1558, 1562-1565.
Metsuyanim et al. "Accumulation of Malignant Renal Stem Cells Is Associated With Epigenetic Changes in Normal Renal Progenitor Genes", Stem Cells, 26: 1808-1817, 2008.
Metsuyanim et al. "Expression of Stem Cell Markers in the Human Fetal Kidney", PLoS ONE, XP002581532, 4(8): e6709-1-e6709-15, Aug. 2009.
Milutinovic et al. "Valproate Induces Widespread Epigenetic Reprogramming Which Involves Demethylation of Specific Genes", Carcinogenesis, 28(3): 560-571, 2007.
Miyamoto et al. "Cell-Free Extracts From Mammalian Oocytes Partially Induce Nuclear Reprogramming in Somatic Cells", Biology of Reproduction, XP002583272, 80(5): 935-943, May 1, 2009. p. 936, 939.
Nishinakamura "Kidney Development Conserved Over Species: Essential Roles of Sall1", Seminars in Cell Development and Biology, 14: 241-247, 2003. Abstract.
Osafune et al. "Identification of Multipotent Progenitors in the Embryonic Mouse Kidney by a Novel Colony-Forming Assay", Development, XP002581530, 133(1): 151-161, Jan. 2006. p. 153, Fig. 1.

(56) References Cited

OTHER PUBLICATIONS

Pode-Shakked et al. "Developmental Tumourigenesis: NCAM as a Putative Marker for the Malignant Renal Stem/Progenitor Cell Population", Journal of Cellular and Molecular Medicine, XP002581529, 13(8B): 1792-1808, Published Online Dec. 16, 2008. p. 1795, r-h col., Fig. 1.
Rivera et al. "Wilm's Tumor: Connecting Tumorigenesis and Organ Development in the Kidney", Nature Reviews: Cancer, 5: 699-712, 2005.
Rosenberg et al. "Stem Cells and the Kidney: Where Do We Go From Here?", Journal of the American Society of Nephrology, XP002581964, 18(12): 3018-3020, Dec. 2007. p. 3019.
Schmelzer et al. "The Phenotypes of Pluripotent Human Hepatic Progenitors", Stem Cells, XP002581966, 24(8): 1852-1858, Aug. 2006.
Schmidt-Ott et al. "WNT/Beta-Catenin Signaling in Nephron Progenitors and Their Epithelial Progeny", Kidney International, XP002602079, 74(8): 1004-1008, Oct. 2008.
Self et al. "Six2 Is Required for Suppression of Nephrogenesis and Progenitor Renewal in the Developing Kidney", The EMBO Journal, 25: 5214-5228, 2006.
Senanayake et al. "The Pluripotent Renal Stem Cell Regulator SIX2 Is Activated in Renal Neoplasms and Influences Cellular Proliferation and Migration", Human Pathology, 44: 336-345, 2013.
Trzpis et al. "Epithelial Cell Adhesion Molecule. More Than a Carcinoma Marker and Adhesion Molecule", The American Journal of Pathology, XP002581967, 171(2): 386-395, Aug. 2007. p. 388-389, Table 2.
Trzpis et al. "Expression of EpCAM Is Up-Regulated During Regeneration of Renal Epithelia", Journal of Pathology, XP002581968, 216(2): 201-208, Oct. 2008.
Weissmann "Translating Stem and Progenitor Cell Biology to the Clinic: Barriers and Opportunities", Science, 287(5457): 1442-1446, Feb. 25, 2000.
Yoshikawa et al. "Inhibition of Histone Deacetylase Activity Suppresses Epithelial-to-Mesenchymal Transition Induced by TGF-[Beta]1 in Human Renal Epithelial Cells", Journal of the American Society of Nephrology, XP002583270, 18(1): 58-65, Jan. 2007. p. 58.
Zhong et al. "Spheres Derived From the Human SK-RC-42 Renal Cell Carcinoma Cell Line Are Enriched in Cancer Stem Cells", Cancer Letters, XP027451196, 299(2): 150-160, Dec. 28, 2010.
Communication Pursuant to Article 94(3) EPC Dated Mar. 27, 2015 From the European Patent Office Re. Application 10710685.8.
Communication Pursuant to Article 94(3) EPC Dated Mar. 27, 2015 From the European Patent Office Re. Application No. 10712582.5.
Communication Pursuant to Article 94(3) EPC Dated Mar. 27, 2015 From the European Patent Office Re. Application No. 11188963.0.
Advisory Action Before the Filing of an Appeal Brief and Examiner-Initiated Interview Summary Dated Jul. 14, 2015 From the US Patent and Trademark Office Re. U.S. Appl. No. 13/697,531.
Office Action Dated Jul. 12, 2015 From the Israel Patent Office Re. Application No. 223017 and Its Translation Into English.
Official Action Dated Oct. 7, 2015 From the US Patent and Trademark Office Re. U.S. Appl. No. 14/027,256.
Hueber et al. "PAX2 Inactivation Enhances Cisplatin-Induced Apoptosis in Renal Carcinoma Cells", Kidney International, 69: 1139-1145, Published Online Feb. 15, 2006.
Nakagawa et al. "Generation of Induced Pluripotent Stem Cells Without Myc From Mouse and Human Fibroblasts", Nature Biotechnology, 26(1): 101-106, Jan. 2008.
Official Action Dated Dec. 2, 2015 From the US Patent and Trademark Office Re. U.S. Appl. No. 13/697,531.
Official Action Dated Feb. 2, 2016 From the US Patent and Trademark Office Re. U.S. Appl. No. 14/027,256.
Communication Pursuant to Article 94(3) EPC Dated Mar. 14, 2016 From the European Patent Office Re. Application No. 11728406.7.
Official Action Dated May 13, 2016 From the US Patent and Trademark Office Re. U.S. Appl. No. 13/697,531.
Office Action Dated Jun. 28, 2016 From the Israel Patent Office Re. Application No. 214837 and Its Translation Into English.
Official Action Dated Oct. 20, 2016 From the US Patent and Trademark Office Re. U.S. Appl. No. 14/027,256.
Communication Pursuant to Article 94(3) EPC Dated Oct. 24, 2016 From the European Patent Office Re. Application 10710685.8.
Communication Pursuant to Article 94(3) EPC Dated Nov. 29, 2016 From the European Patent Office Re. Application No. 11728406.7. (4 Pages).
Official Action Dated Dec. 9, 2016 From the US Patent and Trademark Office Re. U.S. Appl. No. 13/697,531. (11 pages).
Requisition by the Examiner Dated Feb. 2, 2017 From the Canadian Intellectual Property Office Re. Application No. 2,799,307. (34 Pages).

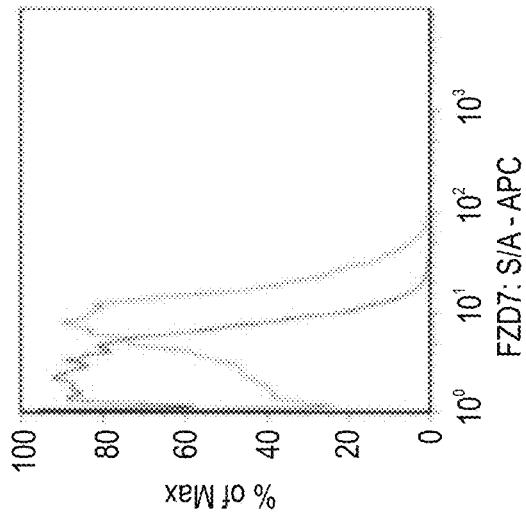
FIG. 2E
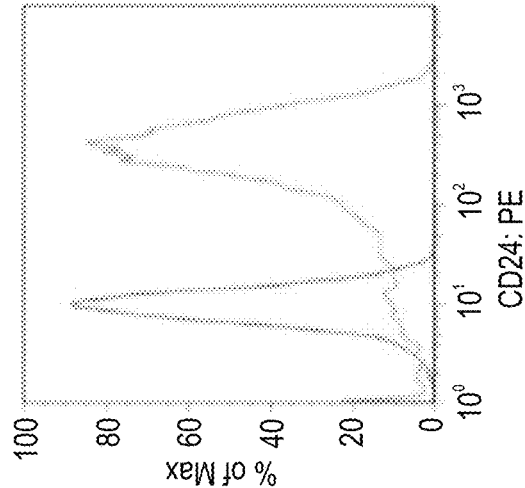
FIG. 2F
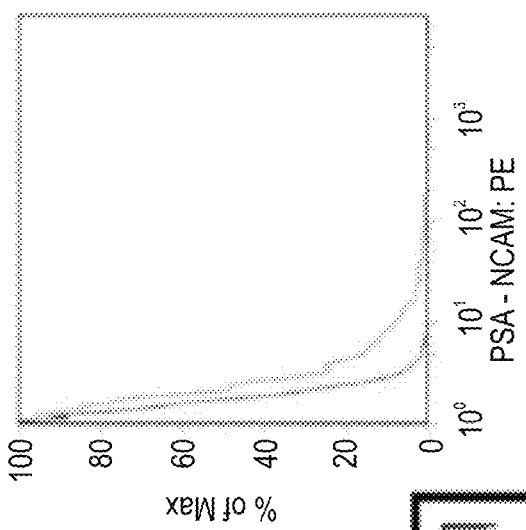
FIG. 2G
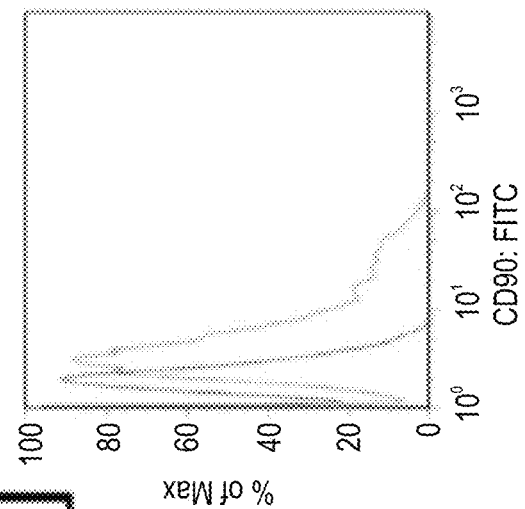
FIG. 2H

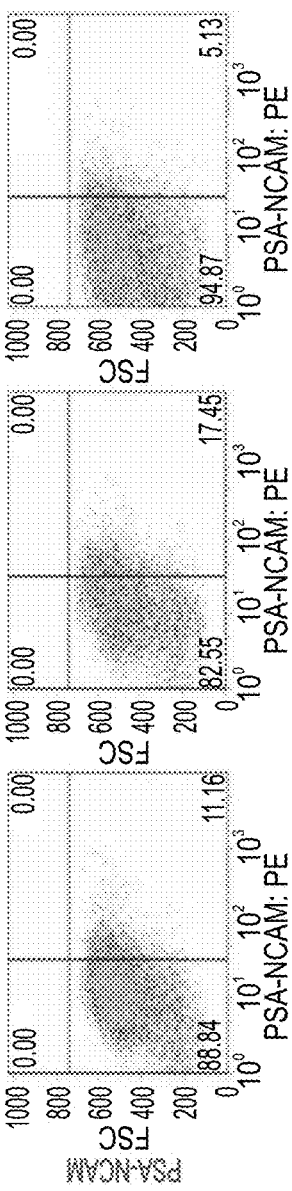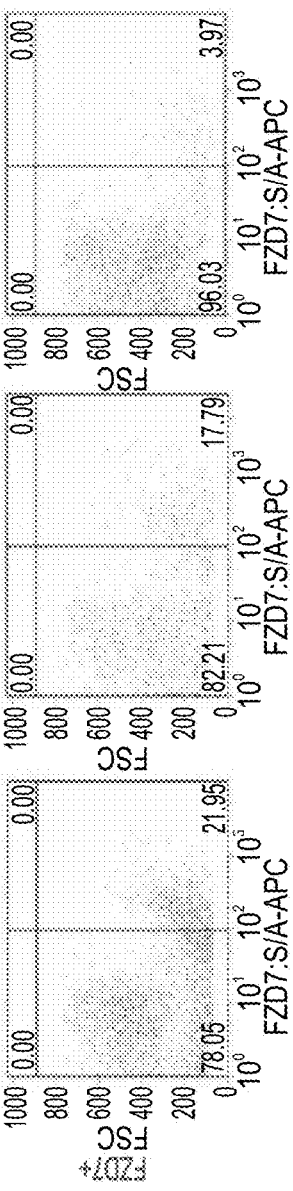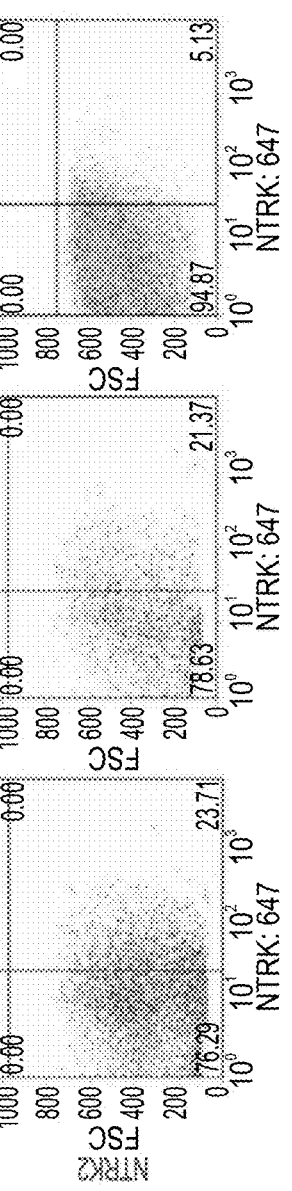

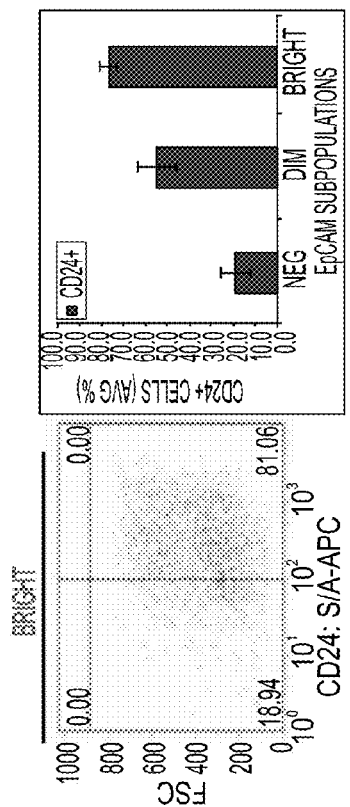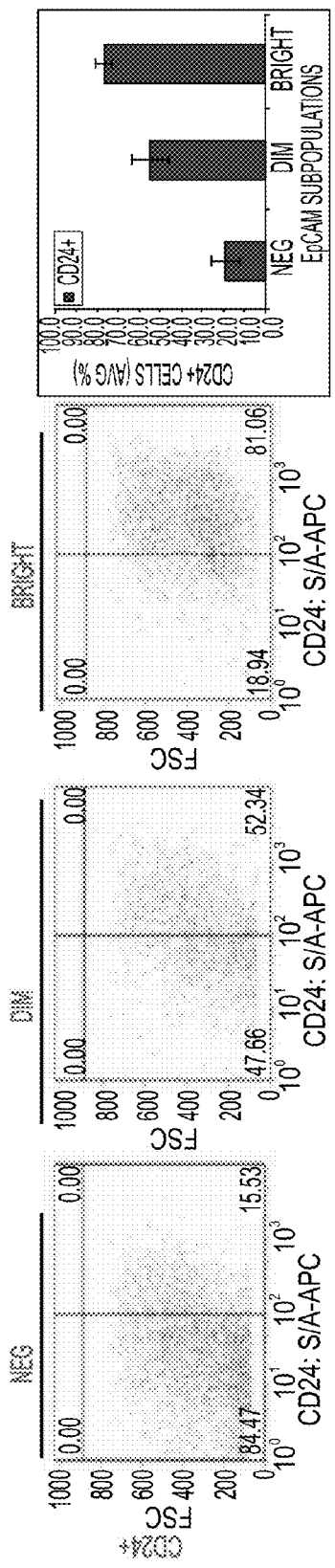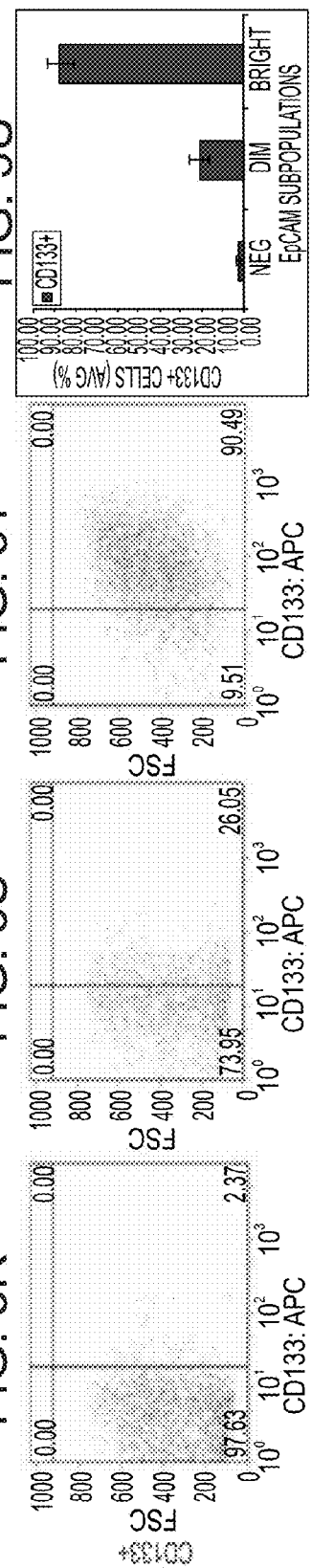
FIG. 3R, FIG. 3S, FIG. 3T, FIG. 3U, FIG. 3V, FIG. 3W, FIG. 3X, FIG. 3Y

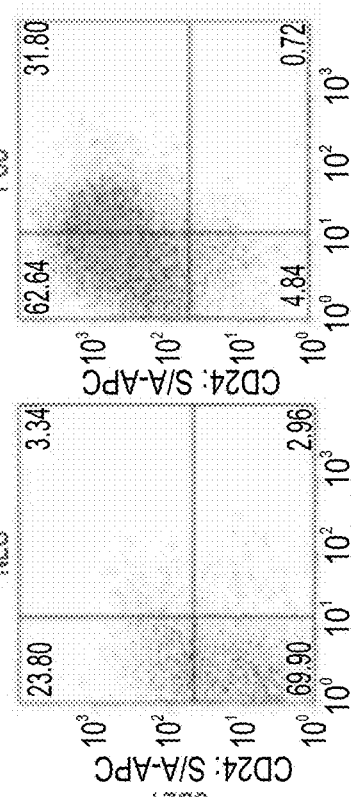
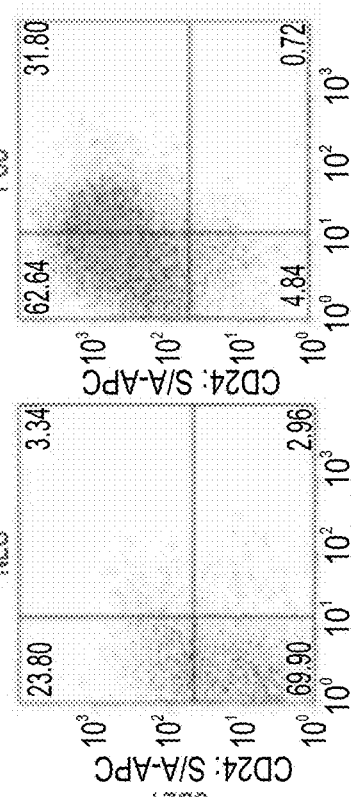
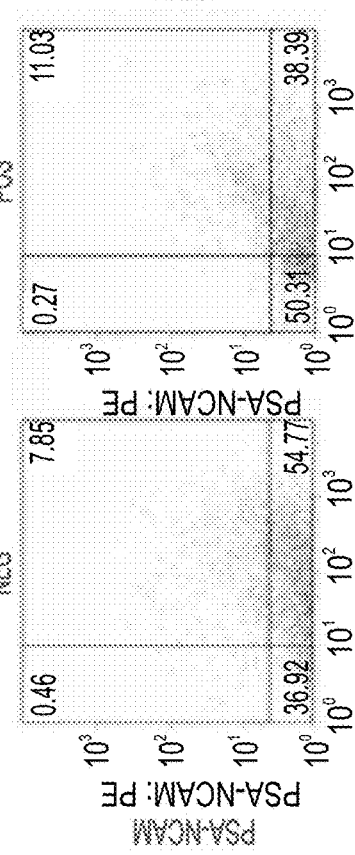
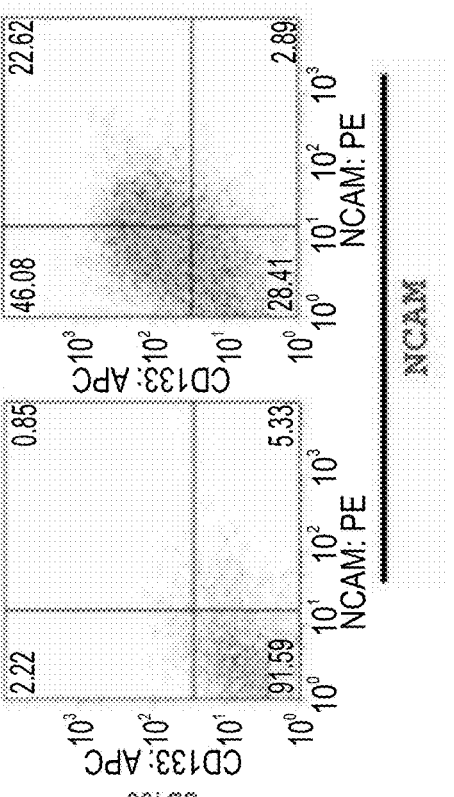
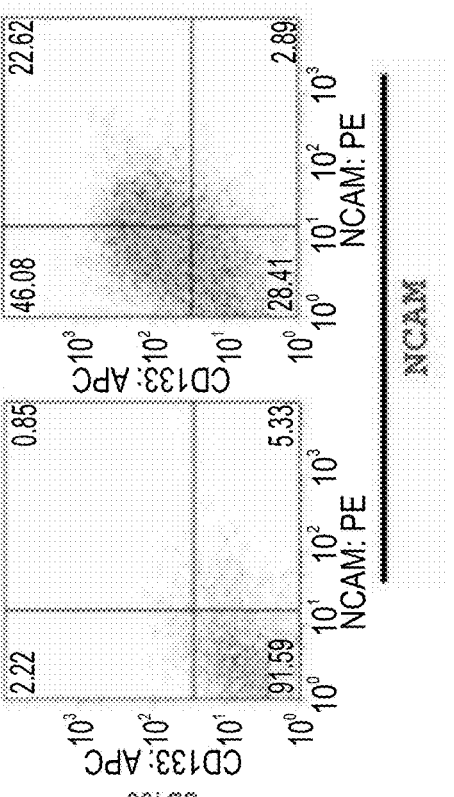
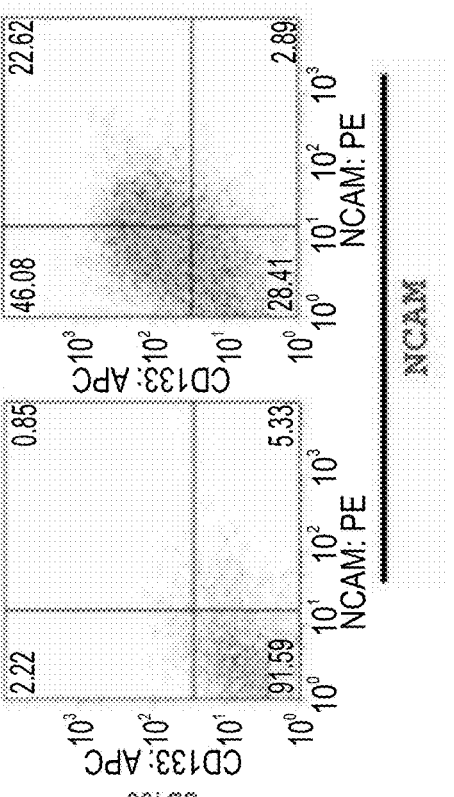
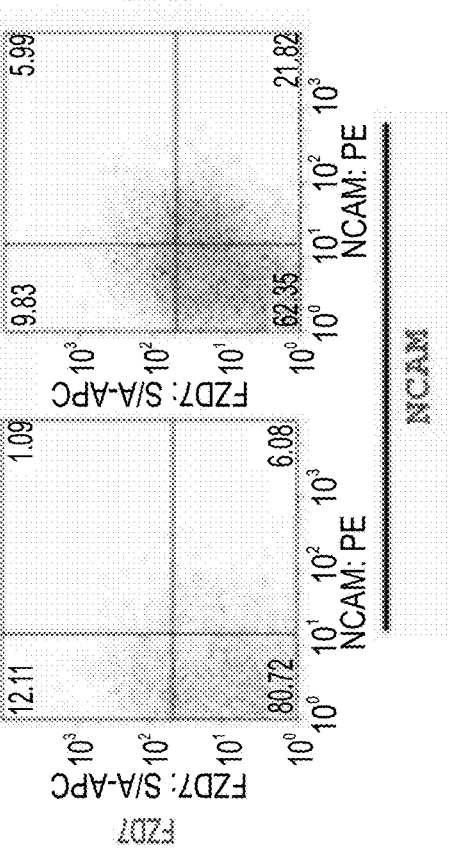

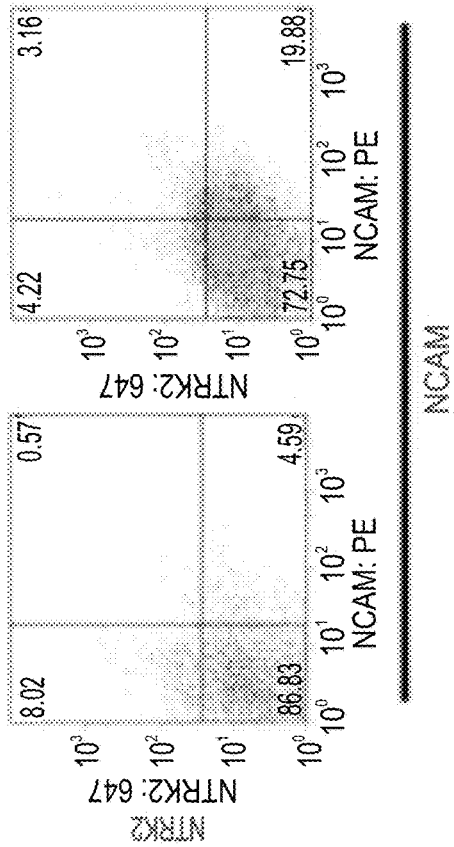
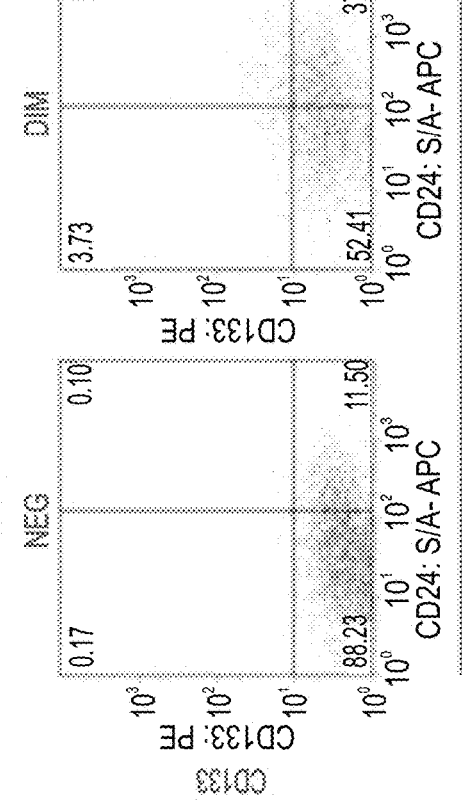
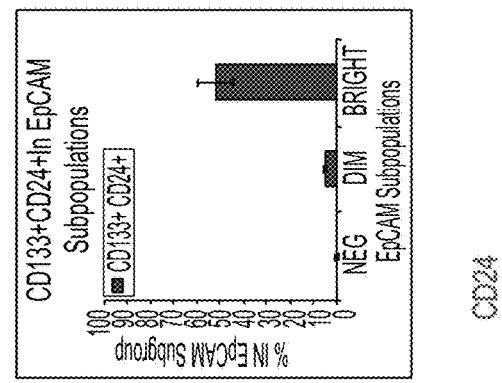

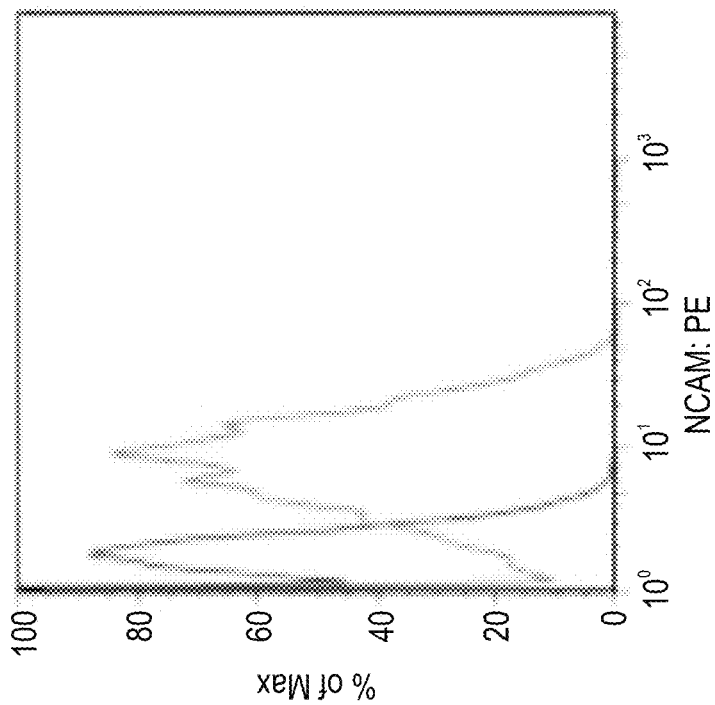
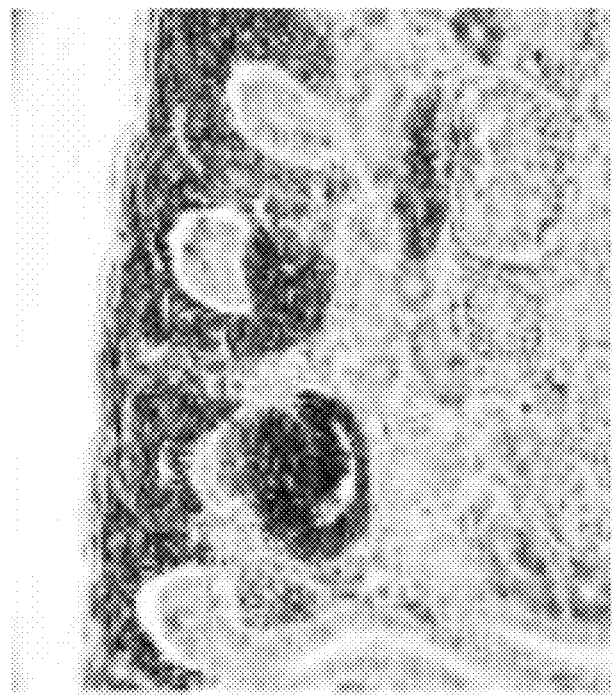

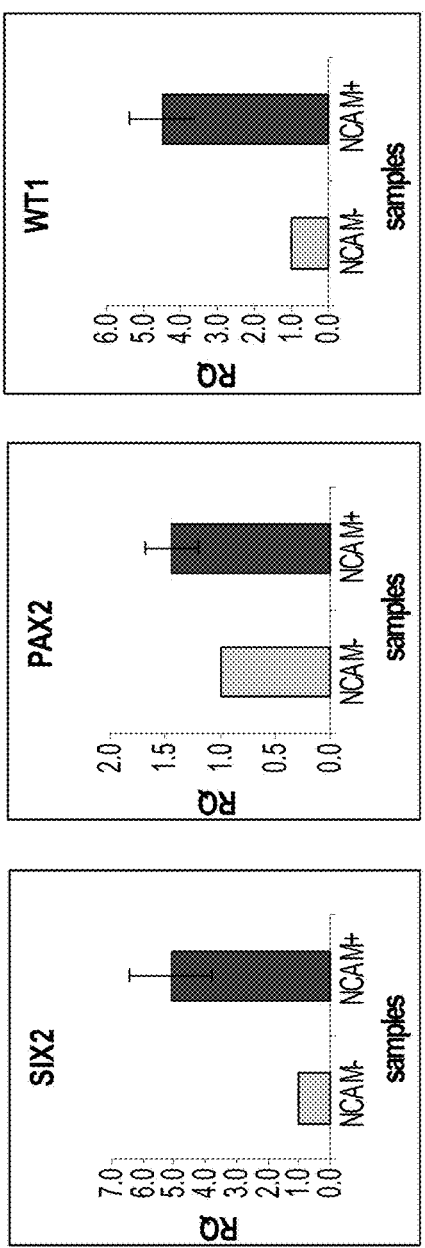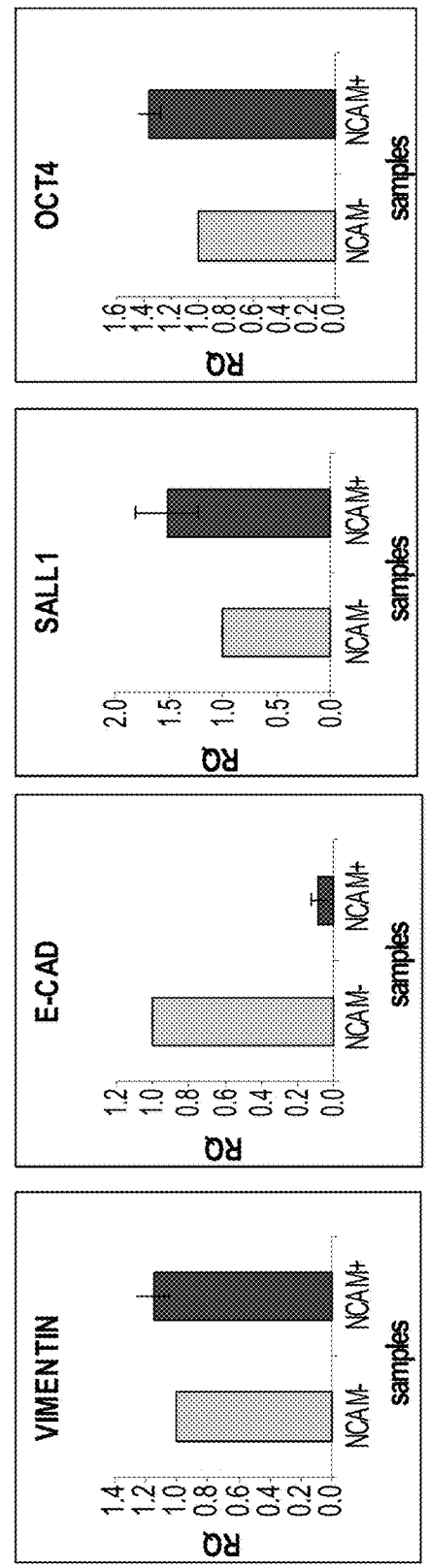

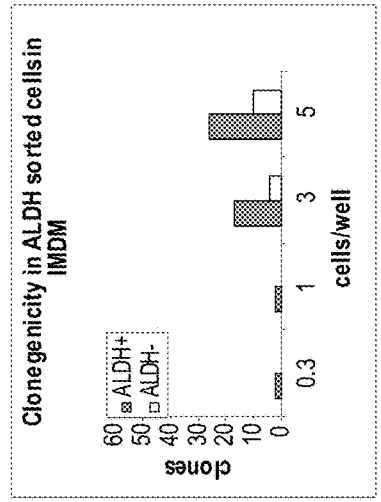
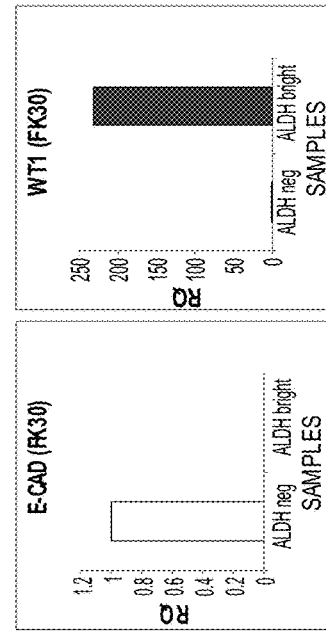
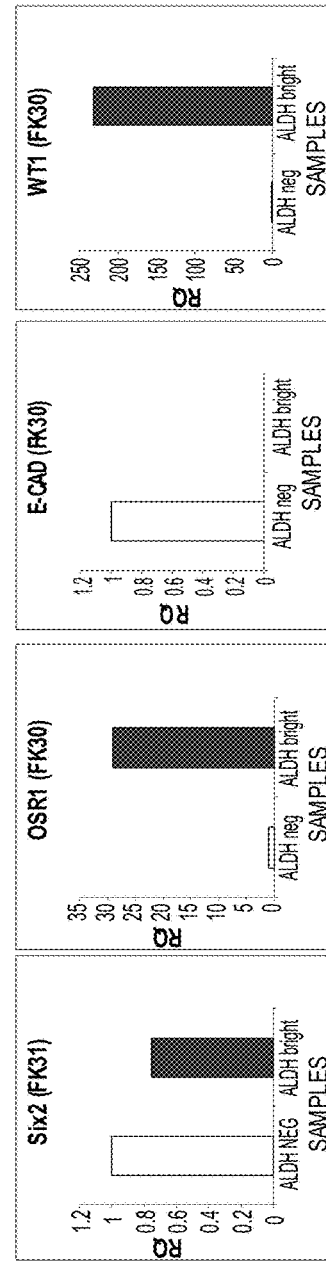
FIG. 13A
FIG. 13B
FIG. 13C
FIG. 13D
FIG. 13E

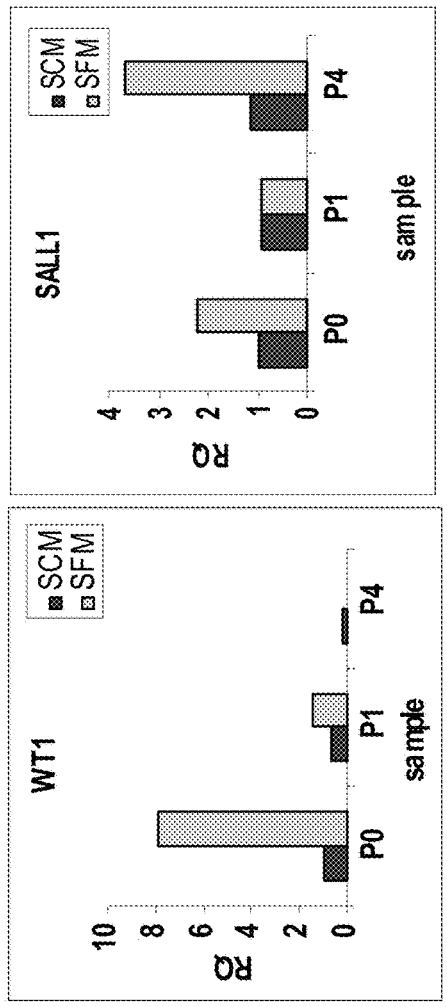
FIG. 15A
FIG. 15B
FIG. 15C
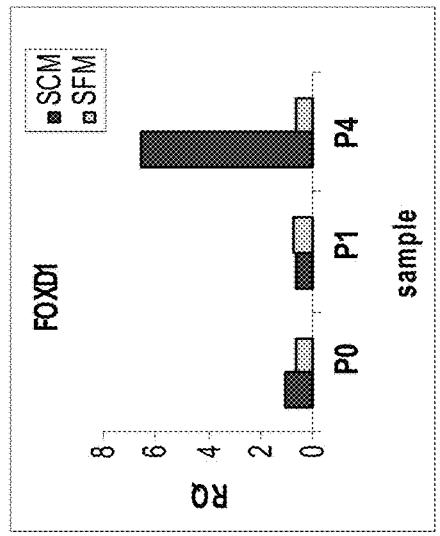
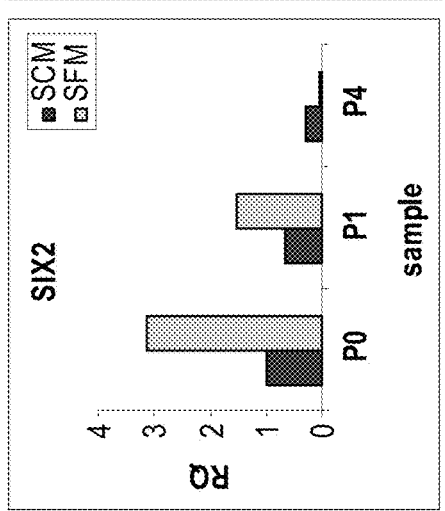
FIG. 15D
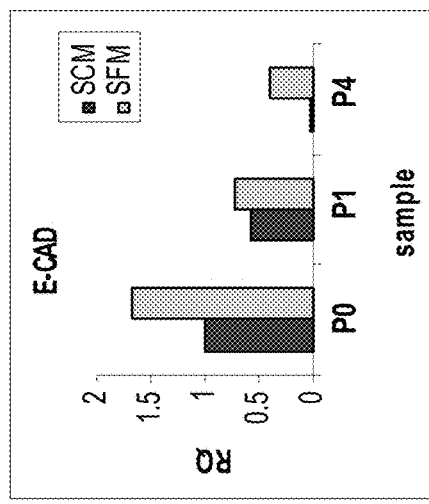
FIG. 15E

US 9,808,488 B2

ISOLATED POPULATIONS OF RENAL STEM CELLS AND METHODS OF ISOLATING AND USING SAME

RELATED APPLICATIONS

This application is a division of U.S. patent application Ser. No. 13/203,282 filed Aug. 25, 2011, which is National Phase of PCT Patent Application No. PCT/IL2010/000158 having International filing date of Feb. 25, 2010, which claims the benefit of priority under 35 USC §119(e) of U.S. of U.S. Provisional Patent Application Nos. 61/202,426 and 61/202,425 both filed on Feb. 26, 2009. The contents of the above applications are all incorporated by reference as if fully set forth herein in their entirety.

FIELD AND BACKGROUND OF THE INVENTION

The present invention, in some embodiments thereof, relates to isolated populations of renal stem cells and methods of isolating and using same.

The kidney is a vital organ in mammals, responsible for fluid homeostasis, waste excretion, and hormone production. There are a variety of possible injuries and disorders including cancer, trauma, infection, inflammation and iatrogenic injuries or conditions that can lead to chronic disease or cause reduction or loss of function of a kidney. The incidence of chronic kidney disease in the United States has reached epidemic proportions, and a significant number of these patients will develop end-stage renal disease (ESRD), with glomerular filtration rates too low to sustain life. Dialysis is the major treatment modality for ESRD, but it has significant limitations in terms of morbidity, mortality, and cost. Allogenic kidney transplantation provides significant benefits in terms of mortality and is ultimately less costly, but is hampered by a severe shortage of available donor organs. Acute renal failure (ARF) is also quite common, having a mortality rate that ranges from 20 to 70%. For a number of reasons, including aggressive care of an older patient population, the mortality rate due to ARF has not changed over the past 20 years despite advances in technology and therapies.

Although kidney disease has a variety of individual types, they appear to converge into a few pathways of disease progression. The functional unit of the kidney is the nephron. There is a decrease in functioning nephrons with the progression of the disease; the remaining nephrons come under more stress to compensate for the functional loss, thereby increasing the probability of more nephron loss and thus creating a vicious cycle. Furthermore, unlike tissues such as bone or glandular epithelia which retain significant capacity for regeneration, it has generally been believed that new nephron units are not produced after birth, that the ability of the highly differentiated tissues and structures of the kidneys have limited reparative powers and, therefore, that mammals possess a number of nephron units that can only decline during post-natal life. There is an increasing interest in developing novel therapies for kidney disease, including artificial organs, genetic engineering, and cell therapy.

The early development of the mammalian metanephros, the direct precursor tissue of the adult kidney, is a complex process that involves highly regulated interactions between two derivatives of the intermediate mesoderm, the wolffian duct and the metanephric/nephrogenic mesenchyme. Reciprocal signaling between the neohrogenic/metanephric mesenchyme and a derivative of the nephric duct known as the ureteric bud results in branching of the ureteric bud (UB) and condensation of metanephric mesenchyme (MM) at its tips (4, 5). The condensed mesenchyme is thought to form a precursor cell population, which both maintains itself at the tips of the UB (via proliferation and/or addition from the surrounding non-condensed mesenchyme) and gives off cells that differentiate into nephrons, the functional filtration unit of the kidney (6). Recent experiments have established that the progenitor cell in the MM fulfils the criteria of a true committed stem cell in that is capable of self-renewing and of differentiating towards different types of nephron epithelia (7-9).

The human metanephros appears at the $5^{th}$ week of gestation and renal stem/progenitor cells in the nephrogenic mesenchyme are induced to form nephrons until 34 weeks of gestation (4, 6). For renal regeneration, both human precursor tissue (10-12) or fetal kidney cell transplantation (13, 14) can be utilized. Isolation of specific human renal progenitors from the nephrogenic mesenchyme requires the characterization of surface markers that would enable cell collection. Given the cellular heterogeneity in the developing human kidney (6), eliminating the unwanted mature cell populations from further cultivation steps, prior to transplantation, would increase the purity of the graft and allow for a better defined cell composition to be transferred.

While the transcriptional program specifying a renal progenitor cell has been thoroughly contemplated (15) corresponding cell surface markers have been hardly studied. Recently, the present inventors performed microarray studies of the human kidney, including adult (AK) and fetal kidneys (FK) and their corresponding tumors, renal cell carcinoma (RCC) and wilms' tumor (WT) (16). Wilms' tumor is classified as a primitive, multilineage malignancy of embryonic renal precursors that are arrested in different stages of differentiation, thus forming in the tumor a cell population similar to condensed mesenchyme (blastema) and also mature epithelial/tubular and stromal cells (17). While fetal kidneys were heterogeneous, WT xenografts were used that by serial passage in mice were highly enriched for blastema at the expense of differentiated elements (16, 18). Genes that were up-regulated in both the stem-like WT xenografts and the human FK were sought, as these were suggested to characterize the progenitor population arising from the MM ('progenitor' genes). Among these were the transcription factors specifying the kidney progenitor cells (7, 15, 19, 20) including WT1, PAX2, LIM1, SIX1, EYA1, SALL1, and CITED1. In addition, various cell surface markers were detected, including NCAM1, ACVRIIB, FZD2, FZD7, GPR39, NTRK2 and DLK1/PREF (16).

U.S. Patent Application 20020102241 discloses Flk-1 positive/Sca-1 negative adult renal stems cells and uses thereof. The cells are described as useful for the regeneration of damaged kidney tissue, the generation of artificial kidneys and the delivery of transgenes.

U.S. Patent Application 20050260623 discloses the identification of adult human stem cells including adult renal stem cells by detecting the expression of Oct-4, and the lack of GJIC activity.

U.S. Patent Application 20070065942 provides human renal stem cells. Also described are human renal stem cells isolated from the papillary region of the human kidney and methods of isolating the same. Also described are methods for culturing, characterizing, and differentiating the same, including methods for identifying human renal stem cells that are positive for Nestin and CD133, and methods for allowing the cells to differentiate into neurons.

Chang, et al., (1987), Cancer Res., 47:1634-1645 teach a method of fetal renal stem cell isolation, based on the cell's contact insensitivity.

Gibson-D'ambrosio et al [In Vitro Cell Dev Biol. 1987 April; 23(4):279-87]teach heterogenic population of cells which may comprise renal stem cells. It is stated that these cells in culture are proximal tubule epithelial cells, indicating that these are in fact differentiated cells and not stem cells.

WO/2005/021738 teaches methods for isolation of kidney stem cells, cells isolated by the methods, and therapeutic uses for those cells. More specifically, the invention relates to isolated kidney-derived progenitor cells that have the potential to differentiate to form cells of any one or all three germ cell layers (endoderm, mesoderm, ectoderm), as well as methods for isolating the cells and for inducing specific differentiation of the cells isolated by the method, and specific markers that are present in these cells such as proteins and transcription factors. Also described are NCAM negative cells.

SUMMARY OF THE INVENTION

According to an aspect of some embodiments of the present invention there is provided a method of isolating renal stem cells, the method comprising enriching for a subpopulation of renal cells from a fetal renal tissue, the subpopulation of renal cells having a NCAM+ signature, wherein the enriching is effected such that at least 80% cells are of the subpopulation of renal cells.

According to some embodiments of the invention, the enriching is effected by detecting surface marker expression of NCAM.

According to some embodiments of the invention, the detecting further comprises detecting surface marker expression of EpCAM.

According to some embodiments of the invention, the method further comprises isolating cells having an EpCAM−/NCAM+ signature.

According to some embodiments of the invention, the method further comprises isolating cells having an EpCAM+/NCAM+ signature.

According to some embodiments of the invention, the method further comprises culturing the subpopulation of renal cells in serum free medium following the enriching.

According to an aspect of some embodiments of the present invention there is provided a method of isolating MM stem cells the method comprising enriching for a subpopulation of renal cells from a fetal renal tissue, the subpopulation expressing a EpCAM−/FZD7+ signature, wherein the enriching is effected such that at least 80% cells are of the subpopulation of renal cells.

According to some embodiments of the invention, the enriching is effected by detecting surface marker expression of EpCAM and FZD7.

According to some embodiments of the invention, the detecting further comprises detecting surface marker expression of NCAM.

According to some embodiments of the invention, the method further comprises isolating cells having an EpCAM−/FZD7+/NCAM− signature.

According to some embodiments of the invention, the method further comprises isolating cells having an EpCAM−/FZD7+/NCAM+ signature.

According to some embodiments of the invention, the method further comprises culturing the subpopulation of renal cells in serum free medium following the enriching.

According to an aspect of some embodiments of the present invention there is provided a method of isolating renal stem cells the method comprising enriching for a subpopulation of renal cells from a fetal renal tissue, the subpopulation of renal cells having a NCAM+/EpCAM+ signature, wherein the enriching is effected such that at least 80% cells are of the subpopulation of renal cells.

According to some embodiments of the invention, the enriching is effected by detecting surface marker expression of NCAM and EpCAM.

According to some embodiments of the invention, the detecting further comprises detecting surface marker expression of a marker selected from the group consisting of FZD7, NTRK and PSA-NCAM.

According to some embodiments of the invention, the method further comprises culturing the subpopulation of renal cells in serum free medium following the enriching.

According to an aspect of some embodiments of the present invention there is provided a method of isolating renal stem cells the method comprising enriching for a subpopulation of renal cells from a fetal renal tissue, the subpopulation of renal cells having a NCAM+/FZD7− signature, wherein the enriching is effected such that at least 80% cells are of the subpopulation of renal cells.

According to some embodiments of the invention, the enriching is effected by detecting surface marker expression of NCAM and FZD7.

According to some embodiments of the invention, the detecting further comprises detecting surface marker expression of EpCAM.

According to some embodiments of the invention, the method further comprises culturing the subpopulation of renal cells in serum free medium following the enriching.

According to an aspect of some embodiments of the present invention there is provided a method of isolating renal stem cells, the method comprising enriching for a subpopulation of renal cells from a fetal renal tissue, the subpopulation of renal cells having a EpCAM+/FZD7+ signature, wherein the enriching is effected such that at least 80% cells are of the subpopulation of renal cells.

According to some embodiments of the invention, the enriching is effected by detecting surface marker expression of EpCAM and FZD7.

According to some embodiments of the invention, the detecting further comprises detecting surface marker expression of NCAM.

According to some embodiments of the invention, the method further comprises culturing the subpopulation of renal cells in serum free medium following the enriching.

According to an aspect of some embodiments of the present invention there is provided a method of isolating renal cells, the method comprising enriching for a subpopulation of renal cells from a fetal renal tissue, the subpopulation of renal cells having a NCAM−/EpCAM+/FZD7− signature, wherein the enriching is effected such that at least 80% cells are of the subpopulation of renal cells.

According to some embodiments of the invention, the enriching is effected by detecting surface marker expression of EpCAM, NCAM and FZD7.

According to an aspect of some embodiments of the present invention there is provided a method of isolating renal cells, the method comprising enriching for a subpopulation of renal cells from a fetal renal tissue, the subpopulation of renal cells having a NCAM−/EpCAM+/CD24+/

CD133+ signature, wherein the enriching is effected such that at least 80% cells are of the subpopulation of renal cells.

According to some embodiments of the invention, the enriching is effected by detecting surface marker expression of EpCAM, NCAM CD24 and CD133.

According to an aspect of some embodiments of the present invention there is provided an isolated population of cells comprising at least 80% fetal renal stem cells having a EpCAM−/FZD7+ signature.

According to some embodiments of the invention, the renal stem cells have a EpCAM−/FZD7+/NCAM− signature.

According to some embodiments of the invention, the renal stem cells have a EpCAM−/FZD7+/NCAM+ signature.

According to an aspect of some embodiments of the present invention there is provided an isolated population of cells comprising at least 80% fetal renal stem cells having a NCAM+ signature.

According to an aspect of some embodiments of the present invention there is provided an isolated population of cells comprising at least 80% fetal renal stem cells having a NCAM+EpCAM− signature.

According to some embodiments of the invention, the fetal renal cells further comprise an EpCAM− signature.

According to an aspect of some embodiments of the present invention there is provided an isolated population of cells comprising at least 80% fetal renal stem cells having a ALDH+ signature.

According to an aspect of some embodiments of the present invention there is provided an isolated population of cells comprising at least 80% MM-derived fetal progenitor cells having a NCAM+/EpCAM+ signature.

According to some embodiments of the invention, the MM-derived progenitor cells further express a surface marker selected from the group consisting of FZD7, NTRK and PSA-NCAM.

According to an aspect of some embodiments of the present invention there is provided an isolated population of cells comprising at least 80% fetal renal stromal cells having a NCAM+/FZD7− signature.

According to some embodiments of the invention, the renal stromal cells have a EpCAM−/NCAM+/FZD7− signature.

According to an aspect of some embodiments of the present invention there is provided an isolated population of cells comprising at least 80% fetal ureteric bud cells having a EpCAM+/FZD7+ signature.

According to some embodiments of the invention, the ureteric bud cells have a EpCAM+/FZD7+/NCAM− signature.

According to an aspect of some embodiments of the present invention there is provided an isolated population of cells comprising at least 80% fetal renal cells having a NCAM−/EpCAM+/FZD7− signature.

According to an aspect of some embodiments of the present invention there is provided an isolated population of cells comprising at least 80% fetal renal cells having a NCAM−/EpCAM+/CD24+/CD133+ signature.

According to an aspect of some embodiments of the present invention there is provided a cell culture comprising a culture medium and any of the isolated population of cells of the present invention.

According to some embodiments of the invention, the cells are seeded on a scaffold.

According to an aspect of some embodiments of the present invention there is provided a method of treating a renal damage in a subject in need thereof comprising administering to the damaged kidney of the subject a therapeutically effective amount of any of the isolated population of cells of the present invention, thereby treating the renal disease in the subject.

According to an aspect of some embodiments of the present invention there is provided a method of identifying an agent capable of regulating differentiation of a renal stem cell, the method comprising contacting any of the isolated population of cells of the present invention with an agent, wherein a change in developmental phenotype is indicative of the agent capable of regulating differentiation of the renal stem cells.

According to an aspect of some embodiments of the present invention there is provided a method of enriching for renal stem cells, the method comprising culturing a population of fetal renal cells in a culture medium devoid of serum, thereby enriching for renal stem cells.

According to some embodiments of the invention, the culturing is effected by culturing a single cell of the population of fetal renal cells in a single container.

According to some embodiments of the invention, the method further comprises selecting a population of fetal renal cells which has a NCAM+ signature prior to the culturing.

According to some embodiments of the invention, the population of fetal renal cells has a NCAM+/EpCAM− signature.

According to some embodiments of the invention, the population of fetal renal cells has a NCAM+/EpCAM+ signature.

According to some embodiments of the invention, the method further comprises selecting a population of fetal renal cells which has a ALDH+ signature prior to the culturing.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIGS. 2A-I are representative flow-cytometry histograms of surface marker molecules (green) EpCAM (FIG. 2A), NCAM1 (FIG. 2B), NTRK2 (FIG. 2C), CD34 (FIG. 2D), PSA-NCAM1 (FIG. 2E), FZD7 (FIG. 2F), CD90 (FIG. 2G), CD24 (FIG. 2H), CD133 (FIG. 2I), and their respective isotype controls (red) in HFK (21 weeks of gestation).

FIGS. 3B-3D, 3F-3H, 3J-3L, 3N-3P, 3R-3T and 3V-3X are representative dot plot graphs of NCAM1 (3B-3D), PSA-NCAM (3F-3H), FZD7 (3J-3L), NTRK2, (3N-3P), CD24 (3R-3T) and CD133 (3V-3X) expression levels in EpCAM subpopulations of HFK. Quadrates were placed according to isotype control confiding the negative staining to the lower left quadrant. Percentage of cells in each subgroup appears on the lower right quadrant.

FIGS. 3E, 3I, 3M, 3Q, 3U and 3Y are summarizing bar graphs of NCAM1 (3E), PSA-NCAM (3I), NTRK2 (3M), FZD7 (3Q), CD24 (3U) and CD133 (3Y) expression levels in EpCAM subpopulations. Data are average % of cells in each subgroup±SD. Analysis of each marker was performed at least three times.

FIGS. 4C-4L are representative dot plot graphs of PSA-NCAM (4C-D), FZD7 (4G-H), NTRK2 (4K-L), CD24 (4E-F) and CD133 (4I-J) co-staining with NCAM in EpCAM positive or negative populations of mid-gestation HFK. Quadrates were placed according to the isotype control confiding the negative staining to the lower left quadrant. Percentage of cells for each quadrant appears in the quadrant.

FIGS. 4M-4O are representative dot plot graphs of CD24 and CD133 co-staining in EpCAM subpopulations of HFK. Quadrates were placed according to the isotype control confiding the negative staining to the lower left quadrant. Percentage of cells for each marker combination appears in the quadrant.

FIG. 4P is a summarizing bar graph of CD24 and CD133 co-staining in EpCAM Subpopulations. Data are average % of cells in each subgroup ±SD. Analysis of each marker was performed at least three times.

FIGS. 10H-N are graphs illustrating gene expression analysis in NCAM subpopulations as measured by quantitative reverse transcription-polymerase chain reaction (qRT-PCR).

FIG. 13A is a graph illustrating that ALDH+ HFK cells have increased clonogenic capabilities.

FIGS. 13B-E are graphs illustrating elevated expression levels of renal progenitor genes in ALDH+ sorted cells compared to ALDH− HFK cells.

FIGS. 15A-E are bar graphs comparing the effect of serum free medium and serum containing medium on nephric progenitor gene expression levels (FIGS. 15A-C), E-cadherin levels (FIG. 15D) and FoxD1 levels which represents stromal differentiation (FIG. 15E) in human fetal kidney cells.

DESCRIPTION OF EMBODIMENTS OF THE INVENTION

Figures 1A, 1B:
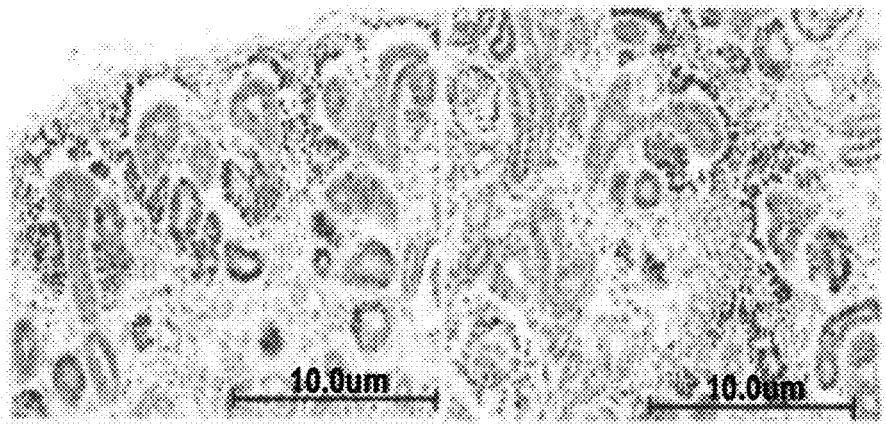
FIGS. 1A-J are photographs illustrating immunostaining of SIX2, NCAM1, FZD7, ACVR2B and NTRK2 in paraffin embedded sections of HFK (12-19 weeks of human gestation); (1A-B) localization of SIX2 to the MM, predominantly to the CM. (C-D) predominant staining of NCAM1 in the MM (including CM) and its derivatives (S- and comma-shaped bodies) and renal stroma, but not mature tubules or UBs. (E-F) FZD7 demonstrates preferential localization to the nephrogenic zone including MM and its derivatives, UBs, and newly forming tubules but not the stroma. (G-H) ACVRIIB immunostaining demonstrates predominant expression in the nephrogenic cortex; MM and its derivatives (S and comma shaped bodies), UBs, parietal epithelium of fetal glomeruli but not in the stroma. (I-J) NTRK2 is detected in the MM (including condensates) and its derivatives, UBs and some differentiated tubules. Figures c, e and g are shown in low magnification (original ×4), FIGS. 1A, B, D, F and H-J are shown in higher magnifications (original ×40; I, original ×20).
Figures 1C, 1D:
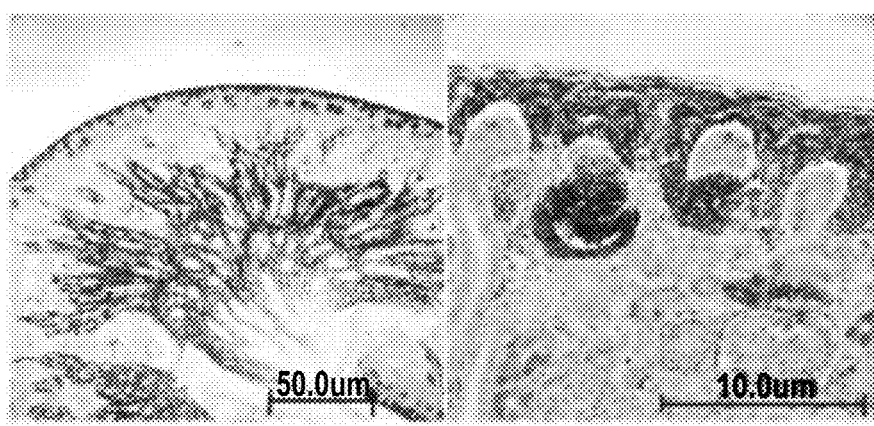

The present invention, in some embodiments thereof, relates to isolated populations of renal stem cells and methods of isolating and using same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Nephrogenesis takes place in a discrete anatomic compartment termed the metanephric mesenchyme (MM) which is comprised of self-renewing renal stem cells that give rise to all cell types of the nephron as well as to pediatric renal cancer (Wilms' tumor) and may prove valuable for renal regeneration after their isolation.

Renal failure, whether arising from an acute or chronic decline in renal function, is a severe condition that can result in substantial or complete failure of the filtration, reabsorption, endocrine and homeostatic functions of the kidney. It is therefore desirable to obtain cells such as stem cells capable of developing into cells that could supply some or all of the functions of the kidney.

While reducing the present invention to practice, the present inventor identified cell surface progenitor markers in human fetal kidney (HFK) which provides for a signature for the isolation of renal stem/progenitor cells. Such a characterization is a major step in the use of stem cells in clinical settings.

Thus, as is illustrated herein below and in the Examples section which follows, the present inventor have used FACS and immunostaining to perform comprehensive profiling of surface antigens up-regulated in a microarray study in both the developing kidney and blastema-enriched stem-like Wilm's tumor xenografts.

No marker was specifically localized to the MM. Nevertheless, FZD7 and NTRK2 were preferentially localized to the nephrogenic zone (MM and emerging tubules), comprised <10% of HFK cells and were mostly present within the EpCAM− and EpCAM$^{dim}$ fractions, indicating putative stem/progenitor markers. In contrast, single markers such CD24 and CD133 as well as double-positive CD24+CD133+ cells comprise >50% of HFK cells and predominantly co-express EpCAM$^{bright}$, indicating they are mostly markers of differentiation. Furthermore, identification of NCAM1 (interchangeably used with NCAM) exclusively in the MM and in MM-derived nephron progenitor structures but also in stroma assisted the present inventors in pinpointing the presence of subpopulations that are putative MM-derived progenitor cells (NCAM+EpCAM+FZD7+), MM stem cells (NCAM+EpCAM−FZD7+) or both (NCAM+FZD7+).

These results provide a feasible approach for experimental cell sorting of human renal progenitors as well as a framework for developing cell selection strategies for renal cell-based therapies.

In addition, the present inventor showed that NCAM+ EpCAM− cells highly overexpressed most MM stem genes (FIGS. 9A-E). Expression of MM stem genes were reduced in sorted NCAM+EpCAM+ (containing putative MM-derived progenitor cells) compared to NCAM+EpCAM− cells but still higher in comparison with the NCAM− cell fraction, indicating a hierarchy for enrichment for the renal 'progenitor' genes. Furthermore, enhanced clonogenic capacity was found for sorted NCAM+ and PSA-NCAM+ cells (FIGS. 11A-B), indicating the presence of stem cells.

Whilst further reducing the present invention to practice, the present inventor unexpectedly found that culturing of fetal renal cells in a serum free medium (SFM) allows for the enrichment of progenitor cells (FIGS. 15A-E). Prior sorting of the fetal renal cells to NCAM+ subpopulations (FIGS. 12A-B) or ALDH+/ALDH$^{bright}$ subpopulations (FIGS. 13A-E) enhanced the clonogenic potential of the cells and stem cell specific marker expression thereof.

Thus according to an aspect of the present invention there is provided an isolated population of cells comprising at least 50%, 60%, 70%, 80%, 90% or more say 100% renal stem cells having a EpCAM−/FZD7+ signature. Such cells are cells composing the metanephric mesenchyme (MM, see FIG. 7) of the renal cortex.

As used herein, the term "isolated" means that a cell population is removed from its natural environment. As used herein, the term "purified," means that a cell population is essentially free from any other cell type (e.g., feeder fibroblasts).

As used herein the term "stem cells" refers to cells which may differentiate to all cell types of the nephron and are typically located in the MM.

As used herein "progenitor cells" can differentiate to certain type of cells in the nephron and are typically located outside the MM.

According to an exemplary embodiment the renal stem cells have a EpCAM−/FZD7+/NCAM− signature. Such cells may be of the loose mesenchyme (LM) in the renal cortex.

According to an exemplary embodiment the renal stem cells have a EpCAM−/FZD7+/NCAM+ signature (or NCAM+/EpCAM−/CD133+/CD24+). Such cells may be of the condensed mesenchyme (CM) in the renal cortex.

Figures 8C, 8D, 8E, 8F:
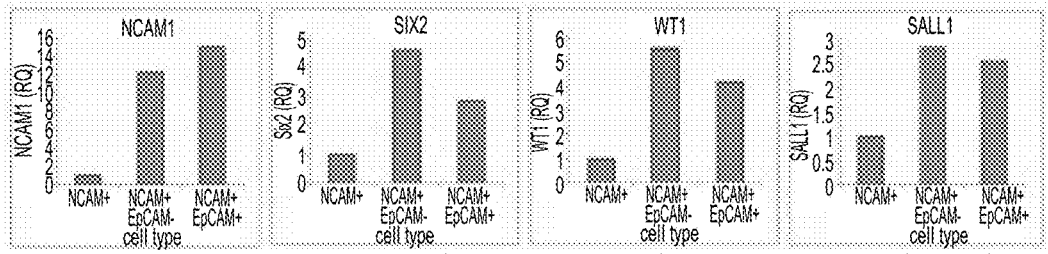
FIGS. 8A-Q show expression of selected genes in NCAM+EpCAM−, NCAM+EpCAM+ as compared to NCAM− populations.
Figures 8G, 8H, 8I, 8J:
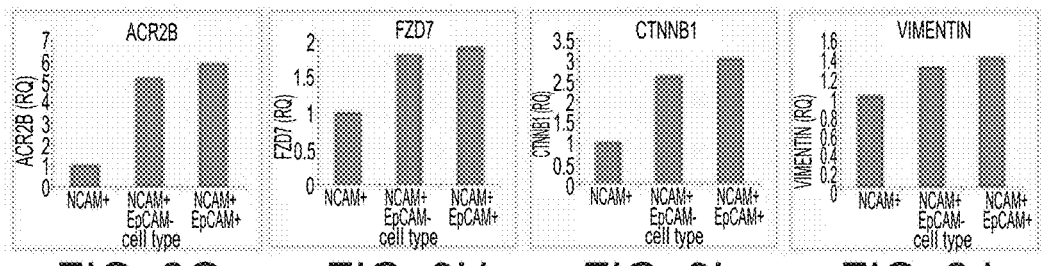
Figures 8K, 8L, 8M, 8N:
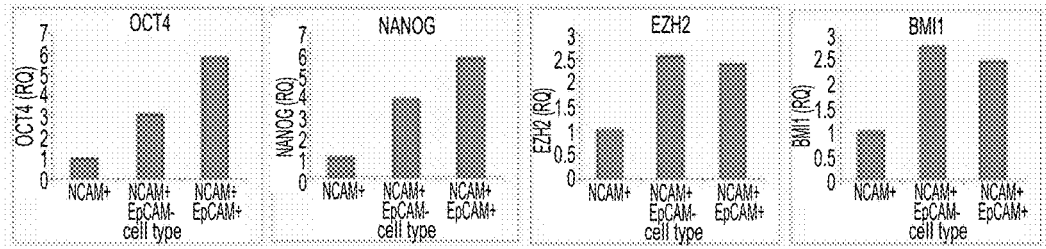
Figures 8O, 8P, 8Q:
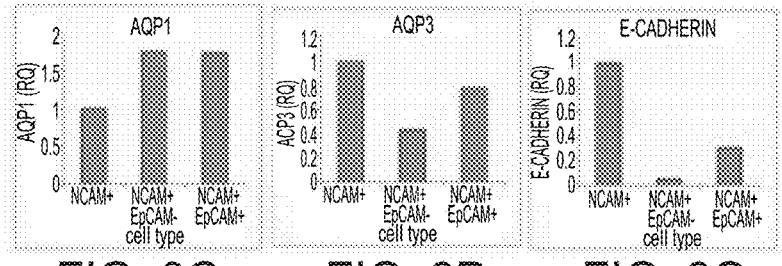

NCAM+ populations of the present invention further comprise a gene expression profile as provided in FIGS. 8C-Q. Assaying expression of any of the genes of the provided expression profile may be used to qualify cells of the NCAM+, NCAM+EpCAM signature.

According to a further aspect of the present invention there is provided an isolated population of cells comprising at least 50%, 60%, 70%, 80%, 90% or more say 100% MM-derived progenitor cells having a NCAM+/EpCAM+ signature.

According to an exemplary embodiment the MM-derived progenitor cells further express a surface marker selected from the group consisting of FZD7, NTRK2 and PSA-NCAM1 as well as ROR2, ACVR2B, CD133 and CD24). These cells typically compose the C and S shape bodies of the fetal kidneys and may differentiate to the nephric tissue (e.g., tubules and glumeruli-visceral and parietal epithelium). These cells are abundant in the fetal kidney but in the tissues of the collective system.

According to a further aspect of the present invention there is provided an isolated population of cells comprising at least 50%, 60%, 70%, 80%, 90% or more say 100% fetal renal cells having a NCAM−/EpCAM+/CD24+/CD133+ signature. These cells are differentiated nephrons.

According to a further aspect of the present invention there is provided an isolated population of cells comprising at least 50%, 60%, 70%, 80%, 90% or more say 100% renal stromal cells having a NCAM+/FZD7− signature. These cells can differentiate to the interstitium (whereby cells of the interstitium comprise NCAM+/EpCAM− signature).

According to an exemplary embodiment the renal stromal cells have a EpCAM−/NCAM+/FZD7− signature.

According to a further aspect of the present invention there is provided an isolated population of cells comprising at least 50%, 60%, 70%, 80%, 90% or more say 100% uretric bud cells having a EpCAM+/FZD7+ signature.

According to an exemplary embodiment the ureteric bud cells have a EpCAM+/FZD7+/NCAM− signature. These cells may differentiate to differentiated cells of the collecting ducts.

Thus, according to a further aspect of the present invention there is provided an isolated population of cells comprising at least 50%, 60%, 70%, 80%, 90% or more say 100% fetal renal cells having a NCAM−/EpCAM+/FZD7− signature.

According to an exemplary embodiment the cells are derived from a fetus, e.g., human fetus. Typically, the nephrogenic zone exists 5-34 weeks of human gestation and cells can be isolated along that time frame. According to an exemplary embodiment the cells are retrieved from a human fetal kidney of mid gestation 14-21 weeks.

As used herein the phrase "renal stem cell" refers to a cell which is not terminally differentiated as a renal cell but which has the ability to differentiate into specialized cell having one or more structural and/or functional aspects of a physiologic kidney. According to specific embodiments the renal stem cells are not embryonic stem cells.

The present invention further provides for a method of isolating the aforementioned cells. This is effected by enriching for a subpopulation of renal cells from a renal tissue (e.g., fetal), the subpopulation of renal cells having any of the above-mentioned surface-marker signature.

Thus a human kidney (e.g., fetal) is provided. The kidney may comprise a whole kidney or fragments thereof (e.g., renal capsule).

Below is a list of some of the exemplary markers of the present invention with their accession numbers.

NCAM1 (3 variants): NM_181351, NM_000615, NM_001076682; EPCAM: NM_002354; FZD7: NM_003507; CD24: NM_013230; CD133 (PROM1): NM_006017; NTRK2: AF410902; PSA-NCAM, Polysialylated NCAM1 same ID as NCAM1; ACVRIIB: NM_001106; ROR2 (2 variants): M97639 NM_004560; oct4 (POU5F1): NM_203289 NM_002701; six2: NM_016932 {accession number: AF136939; sall1: NM_002968; ctnnb1 NM_001098210 (NM_001098209 XM_001133660 XM_001133664 XM_001133673 XM_001133675 NP_001091679 XP_001133660 XP_001133664 XP_001133673 XP_001133675); vimentin: NM_003380 (accession number: M14144); Bmi1: NM_005180 (accession number BC011652); ezh2 (2 variants): NM_152998 NM_004456; nanog: NM_024865 (accession number: AB093576 (complete); aqp1-NM_000385 (accession number: M77829); aqp3: NM_004925; e-cadherin (CDH1): NM_004360 (accession number: L08599).

Antibodies for the above mentioned cell markers are commercially available. Examples include but are not limited to, NCAM1 (eBioscience), EPCAM (MiltenyiBiotec), FZD7 (R&D Systems), CD24 (eBioscience), CD133 (MiltenyiBiotec), NTRK2 (R&D Systems), PSA-NCAM (MiltenyiBiotec) ACVRIIB (R&D Systems), ROR2 (R&D Systems).

As used herein, the term "enriching" refers to a procedure which allows the specific subpopulation of renal cells to comprise at least about 50%, preferably at least about 70%, more preferably at least about 80%, about 95%, about 97%, about 99% or more renal stem cells having the desired signature (e.g. EpCAM−/FZD7+ or NCAM+/EpCAM+).

The enriching may be effected using known cell sorting procedures such as by using a fluorescence-activated cell sorter (FACS).

As used herein, the term "flow cytometry" refers to an assay in which the proportion of a material (e.g. renal cells comprising a particular maker) in a sample is determined by labeling the material (e.g., by binding a labeled antibody to the material), causing a fluid stream containing the material to pass through a beam of light, separating the light emitted from the sample into constituent wavelengths by a series of filters and mirrors, and detecting the light.

A multitude of flow cytometers are commercially available including for e.g. Becton Dickinson FACScan and FACScalibur (BD Biosciences, Mountain View, Calif.). Antibodies that may be used for FACS analysis are taught in Schlossman S, Boumell L, et al, [Leucocyte Typing V. New York: Oxford University Press; 1995] and are widely commercially available.

It will be appreciated that the enriching may also be effected by depleting of non-relevant subpopulations such as renal stromal cells or interstitium (interstitial) cells having a cell surface signature as described herein.

Once isolated, cells of the present invention may be cultured and allowed to proliferate in serum free medium (SFM) in order to preserve their stem/progenitor cell phenotype. Optionally the cells may be directed to differentiate into a desired lineage.

The present inventors have found that culturing fetal renal cells in SFM allows for the enrichment of a renal progenitor cell population, as evidenced by enhancement of stem-cell associated genes and enhancement of clonogenicity (see Examples 3 and 4 herein below). The present inventors showed that serum containing media results in unwanted effects of stromal expansion at the expense of stem/progenitor cells.

Thus, according to another aspect of the present invention there is provided a method of enriching for renal stem cells, the method comprising culturing a population of fetal renal cells in a culture medium devoid of serum, thereby enriching for renal stem cells.

A contemplated culture medium is IMDM (Invitrogen) or DMEM (Invitrogen).

According to one embodiment, the fetal renal cells are cultured following a limiting dilution assay, where a single cell is cultured individually in a single container (e.g. a single cell is cultured in one well of a 96 well plate).

Pre-selecting for a particular cell population prior to culture in serum-free medium may aid in enhancing the purity of the isolated stem cell populations. Thus the present invention contemplates pre-selecting fetal renal cells which have a NCAM+ signature, a NCAM+/EpCAM− signature, a NCAM+/EpCAM+ signature or an ALDH+ signature.

According to another embodiment a particular cell population may be selected following culture in SFM. Thus the present invention contemplates post-selecting fetal renal cells which have a NCAM+ signature, a NCAM+/EpCAM− signature, a NCAM+/EpCAM+ signature or an ALDH+ signature.

Accordingly, the present invention contemplates pure populations (more than 80%, more than 85%, more than 90%, more than 91%, more than 92%, more than 93%, more than 94%, more than 95%, more than 96%, more than 97%, more than 98%, more than 99%, more than 99.5%, or even 100%) of renal stem and/or progenitor cells having a NCAM+ signature, a NCAM+/EpCAM+ signature, NCAM+/EpCAM− or an ALDH+ signature.

In order to confirm the presence of renal stem cells, the cells may be tested for expression of stem cell-specific genes. An upregulation of such genes infers the presence of renal stem cells. Such genes include, but are not limited to Six2 (NM_016932-accession number: AF136939), osr1 (NM_145260.2), Pax2 (NM_003987.3 NM_000278.3, NM_003988.3, NM_003989.3, NM_003990.3), Sall1 (NM_002968) and Cited 1 (NM_001144885.1, NM_001144886.1, NM_001144887.1 NM_004143.3). Methods for analyzing for the expression of stem cell-specific genes include RT-PCR, Northern blot, Western blot, flow cytometry and the like. Since clonogenicity is a function of stem cells, another way to confirm the presence of renal stem cells is to analyze the clonogenic potential of the cells, as described in Example 3, herein below.

Cells of the present invention can be genetically modified to express a transgene. This may be used to increase survival of the cells, render them immortalized or differentiated to a desired lineage. Examples of such transgenes and methods of introducing the same are provided below.

Candidate genes for gene therapy include, for example, genes encoding the alpha 5 chain of type IV collagen (COL4A5), polycystin, alpha-galactosidase A, thiazide-sensitive sodium chloride cotransporter (NCCT), nephrin, actinin, or aquaporin 2.

Further, genes encoding erythropoeitin or insulin can be introduced into a kidney stem cell. For treatment of anemia associated with renal failure or diabetes it can be useful to introduce into a patient a stem cells modified to express erythropoeitin or insulin. The renal stem cells can be stably or transiently transfected with DNA encoding any therapeutically useful polypeptide.

The renal stem cells of the invention can also be provided with a transgene encoding VEGF or some other factor that can promote growth and or differentiation of cells.

These genes can be driven by an inducible promoter so that levels of enzyme can be regulated. These inducible promoter systems may include a mutated ligand binding domain of the human estrogen receptor (ER) attached to the protein to be produced. This would require that the individual ingest tamoxifen to allow expression of the protein. Alternatives are tetracyclin on or off systems, RU486, and a rapamycin inducible system. An additional method to obtain relatively selective expression is to use tissue specific promoters. For instance, one could introduce a transgene driven by the KSP-cadherin, nephrin or uromodulin-specific promoter.

Cells isolated by the method described herein can be genetically modified by introducing DNA or RNA into the cell by a variety of methods known to those of skill in the art. These methods are generally grouped into four major categories: (1) viral transfer, including the use of DNA or RNA viral vectors, such as retroviruses (including lentiviruses), Simian virus 40 (SV40), adenovirus, Sindbis virus, and bovine papillomavirus for example; (2) chemical transfer, including calcium phosphate transfection and DEAE dextran transfection methods; (3) membrane fusion transfer, using DNA-loaded membrane vesicles such as liposomes, red blood cell ghosts, and protoplasts, for example; and (4) physical transfer techniques, such as microinjection, electroporation, or direct "naked" DNA transfer. Cells can be genetically altered by insertion of pre-selected isolated DNA, by substitution of a segment of the cellular genome with pre-selected isolated DNA, or by deletion of or inactivation of at least a portion of the cellular genome of the cell. Deletion or inactivation of at least a portion of the cellular genome can be accomplished by a variety of means, including but not limited to genetic recombination, by antisense technology (which can include the use of peptide nucleic acids, or PNAs), or by ribozyme technology, for example. Insertion of one or more pre-selected DNA sequences can be accomplished by homologous recombination or by viral integration into the host cell genome. The desired gene sequence can also be incorporated into the cell, particularly into its nucleus, using a plasmid expression vector and a nuclear localization sequence. Methods for directing polynucleotides to the nucleus have been described in the art. The genetic material can be introduced using promoters that will allow for the gene of interest to be positively or negatively induced using certain chemicals/drugs, to be eliminated following administration of a given drug/chemical, or can be tagged to allow induction by chemicals (including but not limited to the tamoxifen responsive mutated estrogen receptor) for expression in specific cell compartments (including but not limited to the cell membrane).

Calcium phosphate transfection, which relies on precipitates of plasmid DNA/calcium ions, can be used to introduce plasmid DNA containing a target gene or polynucleotide into isolated or cultured cells. Briefly, plasmid DNA is mixed into a solution of calcium chloride, then added to a solution which has been phosphate-buffered. Once a precipitate has formed, the solution is added directly to cultured cells. Treatment with DMSO or glycerol can be used to improve transfection efficiency, and levels of stable transfectants can be improved using bis-hydroxyethylamino ethanesulfonate (BES). Calcium phosphate transfection systems are commercially available (e.g., ProFection from Promega Corp., Madison, Wis.).

DEAE-dextran transfection, which is also known to those of skill in the art, may be preferred over calcium phosphate transfection where transient transfection is desired, as it is often more efficient.

Since the cells of the present invention are isolated cells, microinjection can be particularly effective for transferring genetic material into the cells.

The developmental potential of stem cells thus obtained can be investigated using methods which are well known in the art. For example by injection into other organs (liver, muscle, heart and bone marrow) to test their multipotency Clarke et al. describes protocols for investigating the development potential of stem cells (Clarke et al. 2000 Science 288:1660).

The renal stem cells of the invention can be used to supplement or substitute for kidney cells that have been destroyed or have reduced function. Thus, they can be used to treat patients having poor or no kidney function. The renal stem cells of the invention or cells derived from the renal stem cells of the invention may be capable of performing the filtration and reabsorptive/secretive functions of the kidney.

Thus according to an aspect of the present invention there is provided a method of treating a renal damage in a subject in need thereof comprising administering to the damaged kidney of the subject a therapeutically effective amount of any of the isolated population of cells, thereby treating the renal disease in the subject.

Cells of the present invention can be used to treat any form of acute or chronic kidney disease, diabetic nephropathy, renal disease associated with hypertension, hypertensive acute tubular injury (ischemic, toxic), interstitial nephritis, congenital anomalies (Aplasia/dysplasia/obstructive uropathy/reflux nephropathy); hereditary conditions (Juvenile nephronophtisis, ARPCKD, Alport, Cystinosis, Primary Hyperoxaluria); Glomerulonephritides (Focal Segmental Glomerulosclerosis); Multisystem Diseases (SLE, HSP, HUS).

The cells may be administered per se or as part of a pharmaceutical composition where they are mixed with a suitable carrier or excipient.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the renal progenitor cells (or cells differentiated therefrom) accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

The renal stem cells or cells derived from the renal stem cells can be administered into a subject such as surgically or by infusion. For example, renal stem cells are injected in vivo into a kidney that is in the postischemic recovery phase. This can be tested easily in an animal model predictive of ischemic kidney damage, the renal pedicle of an anesthetized mouse is clamped for 30 minutes to induce kidney ischemia. Renal stem cells are then injected into the juxtamedullary region (approximately 2000 cells at a depth of 2-4 mm) After 2 weeks of recovery, immunohistochemical analysis is used as described above to look for differentiated cells surface markers GP330, Tamm-Horfall, Dolichos Biflorous, and the like. Post-incorporation differentiation status can then be compared to pre-injection marker status.

The stem cells of the invention, or cells derived from the stem cells of the invention (e.g., epithelial cells endothelial cells, mesangial cells, vascular smooth muscle cells, and pericytes) can be used to construct artificial kidney systems. Such a system can be based on a hollow fiber filtration system.

In one example of a filtration device, the stem cells of the invention or differentiated progeny thereof are grown on the interior of hollow fibers having relatively high hydraulic conductivity (i.e., ultrafiltration coefficient). The hollow fiber passes through a chamber that is provided with a filtrate outlet port. Arterial blood containing metabolic waste and other unwanted material is introduced into one end of the hollow fiber through an inlet port. Blood passed through the fiber and exits the other end of the fiber through an outlet port where it passed into the patient's vascular venous flow. As blood passes through the fiber, filtrate pass through the cells lining the interior of the fiber and through the hollow fiber itself. This filtrate then passes out of the chamber containing the fiber through the filtrate outlet port. The device preferably includes many such hollow fibers each of which can be in its own chamber. Alternatively many, many hollow fibers (100-100,000 or even more) can be bundled together in a single chamber.

The cells of the invention can be used to create a tubule-processing device. In such a device the stem cells of the invention or differentiated cells derived from the stem cells of the invention can be grown in a layer on the exterior of the semipermeable hollow fiber. The fiber is placed in a chamber that is provided with an inlet port and an outlet port. As ultrafiltrate from filtered blood flows through the chamber, reabsorbant passes through the cell layer and through the wall of the fiber into the lumen of the fiber from which it can be directed back into the patient's systemic circulation. Ultrafiltrate that is not reabsorbed passes through the outlet port of the chamber.

In the devices described above, it can be desirable to coat the fiber surface that will bear the cell layer with extracellular matrix components. For example, the fiber can be coated with materials such as collagen (e.g., Type I collagen or Type IV collagen), proteoglycan, fibronectin, and laminin or combinations thereof. It can be desirable to combine various cell types on the inner or outer surface of the fibers. For example, it can be desirable to include endothelial cells and pericyte, vascular smooth muscle cells or mesangial cells or fibroblasts or combinations thereof. It can also be useful to provide a feeder layer of cells, e.g., irradiated fibroblasts or other cells that can provide soluble factors and structural support to cells they are indirectly or directly in contact with.

The above-described filtration system and the above-described tubule processing system can be combined to create an artificial kidney. Such systems are described in U.S. Pat. No. 6,150,164, hereby incorporated by reference. A number of suitable materials for forming the hollow fiber are described in U.S. Pat. No. 6,150,164, hereby incorporated by reference.

The present invention provides a method of using renal stem cells or progenitor cells to characterize cellular responses to biologic or pharmacologic agents involving isolating the cells as described s, culture expanding the cells to establish a plurality of MRPC cultures, contacting the MRPC cultures with one or more biologic or pharmacologic agents, identifying one or more cellular responses to the one or more biologic or pharmacologic agents, and comparing the one or more cellular responses of the cultures. Tissue culture techniques known to those of skill in the art allow mass culture of hundreds of thousands of cell samples from different individuals, providing an opportunity to perform rapid screening of compounds suspected to be, for example, teratogenic or mutagenic.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Determination of Cell Surface Progenitor Markers in Human Fetal Kidneys

Materials and Methods

Establishment of a Primary Culture from Human Fetal Kidney (HFK):

HFK samples were retrieved from aborted fetuses.

Collected human fetal kidney cells (HFK) were washed with cold HBSS (Invitrogen, Carlsbad, Calif., USA) and minced into ~1 mm cubes using sterile surgical scalpels. The dissected tissue was then incubated for 2 hours at 37° C. with Iscoves's Mod Dulbecco's Medium (IMDM) (Invitrogen) supplemented with 0.1% collagenase II (Invitrogen). The digested tissue was then gradually forced through a 100 μm, 70 μm and 50 μm cell strainer to achieve a single cell suspension, and after removal of the digesting medium resuspended in growth medium [IMDM containing 10% fetal bovine serum (Invitrogen), 100 ng/ml EGF, 100 ng/ml bFGF and 10 ng/ml SCF (R&D Systems, Inc, Minneapolis, USA)] and plated in flasks. Cells were incubated at 37° C. and 5% $CO_2$. Medium was replaced every day for the first 2 days and then every 3-4 days. Cells were passed upon reaching confluence using 0.05 Trypsin/EDTA (Invitrogen) to detach them from the plate. Cells were passed for up to 3 passages and cryo-preserved in FBS with 10% DMSO (Sigma-Aldrich, St Louis, Mo., USA).

IHC Staining of HFK

Immunostaining was performed as previously described[21]. Briefly, 4 μm sections of HFKs (12 or 19 weeks of gestation) were mounted on super frost/plus glass (Menzel, Glazer, Braunschweig, Germany) and processed by the labeled—(strept) avidin-biotin (LAB-SA) method using a histostain plus kit (Zymed, San Francisco, Calif., USA). Heat-induced antigen retrieval was performed by controlled microwave treatment using an H2800 model processor (Energy Bean Sciences, INC) in 10 mM citrate buffer, PH 6.0 for 10 min at 97° C. The sections were treated with 3% $H_2O_2$ for 10 minutes and stained for EZH2 (Zymed), CD56 (Ancell Corporation), CD90 (AbD serotec), DLK1 (Ray Biotec), CD24, GPR39, CD133 (abcam), SIX2 (ABNOVA), FZD7, FZD2 (NOVUS biologicals), ACRIIB and NTRK1 (R&D Systems). Negative control incubations were performed by substituting non-immune serum for the primary antibody. Biotinylated second antibody was applied for 10 minutes followed by incubation with horseradish peroxidase-conjugated streptavidin (HRP-SA) for 10 minutes. Following each incubation, the slides were washed thoroughly with Optimax wash buffer (Biogenex). The immunoreaction was visualized by an HRP-based chromogen/substrate system, including DAB (brown) chromogen (liquid DAB substrate kit—Zymed). The sections were then counterstained with Mayer's hematoxylin, dehydrated and mounted for microscopic examination. Antibody details are provided in Table 1, herein below.

TABLE 1

| Antibody | Marker Identified | Manufacturer | Catalog # |
| --- | --- | --- | --- |
| Rabbit anti EZH2 | EZH2 | Zymed, San Francisco, CA | SKU#36-6300 |
| Monoclonal anti-human CD56 (NCAM1) | CD56 | Ancell Corporation, Bayport, MN, USA | 208-020 |
| Mouse anti-human CD90 | CD90, thy 1 | AbD serotec, Kidlington, Oxford, UK | MCA90 |
| Mouse anti- Preadipocyte factor-1 | DLK1, PREF1 | Ray Biotec, Inc, Parkway Lane, Norcross GA | NR-08-0034 |
| Mouse monoclonal CD24 | CD24 | abcam, Cambridge, UK. | ab31622 |
| Six2 monoclonal antibody | SIX2 | ABNOVA, Walnut, USA | H000010736-M01 |
| Rabbit polyclonal anti frizzled-7 | FZD7 | NOVUS biologicals, Littleton, USA | NLS4900 |
| Rabbit polyclonal anti frizzled-2 | FZD2 | NOVUS biologicals, Littleton, USA | NLS3488 |
| Monoclonal anti-human Activin RIIB antibody | ACRIIB | R&D Systems, Inc, Minneapolis, USA | MAB3393 |
| Rabbit polyclonal to GPCR GPR39 | GPR39 | abcam, Cambridge, UK. | ab39283 |
| Rabbit polyclonal to CD133 | CD133 | abcam, Cambridge, UK. | ab16518 |
| Monoclonal anti-human TrkB antibody | NTRK1 | R&D Systems, Inc, Minneapolis, USA | MAB3971 |

Flow Cytometry.

Cells were detached from culture plated with non-enzymatic cell dissociation solution (Sigma-Aldrich) and a viable cell number was determined using Trypan blue assay (Invitrogen). Cells ($1\times10^5$ in each reaction) were suspended in 50 μl of FACS buffer [0.5% BSA and 0.02% sodium azide in PBS (Sigma-Aldrich and Invitrogen, respectively)] and blocked with FcR Blocking Reagent (MiltenyiBiotec) and human serum (1:1) for 15 minutes at 4° C. Cells were then incubated for 45 minutes with a primary antibody for CD24, NCAM1, C-KIT (all from eBioscience), Thy-1, CD90 (both from BD Pharmingen), CD34, CD133, EpCAM, PSA-NCAM (all from MiltenyiBiotec), ACVR2B, FZD7 or NTRK1 (all from R&D Systems) or a matching isotype control.

Antibodies used in the flow cytometry assays are provided in Table 2, herein below.

TABLE 2

| Antibody | Marker identified | Isotype control | Manufacturer | Catalog # |
|---|---|---|---|---|
| CD24-PE | CD24 | Mouse IgG1 | eBioscience San Diego, USA | 12-0247 |
| Biotin anti-human CD24 | CD24 | Mouse IgG1 | eBioscience | 13-0247 |
| FITC anti-human CD34 | CD34 | Mouse IgG2a | MiltenyiBiotec | 130-081-001 |
| PE anti-human CD56 (N-CAM, NCAM1) | NCAM1 | Mouse IgG2a, κ | eBioscience | 12-0569 |
| FITC mouse anti-human CD90 | Thy-1 | Mouse IgG1, κ | BD Biosciences, San Jose, USA | 555595 |
| CD133/1 (AC133)-APC | CD133 | Mouse IgG1 | MiltenyiBiotec | 130-090-826 |
| CD326 (EpCAM)- FITC | EpCAM | Mouse IgG1 | MiltenyiBiotec | 130-080-301 |
| Monoclonal anti-human Activin RIIB antibody | ACR2B | Mouse IgG1 | R&D Systems, Inc. | MAB3393 |
| Biotinylated anti-human/ mouse Frizzled-7 antibody | FZD7 | rat IgG2A | R&D Systems, Inc. | BAM1981 |
| FITC mouse anti-Human CD90 | CD90 | Mouse IgG1, κ | BD Pharmingen | 555595 |
| Affinity Purified antihuman CD117 (cKit) | C-KIT | Mouse IgG1, κ | eBioscience | 141179 |
| Monoclonal anti-human TrkB antibody | NTRK1 | Mouse IgG1 | R&D Systems, Inc. | MAB3971 |
| Anti- PSA-NCAM-PE | PSA-NCAM | Mouse IgM | MiltenyiBiotec | 130-093-274 |

Cells were washed with FACS buffer, and incubated for 30 minutes at 4° C. with a secondary Ab if needed [Avidin-Fluorescein, APC Streptavidin (both from BD Biosciences) or Alexa Fluor 647 goat anti mouse Alexa Fluor 488 goat anti mouse (both from Invitrogen)]. Cells viability was tested using 7AAD viability staining solution (eBioscience).

Details of secondary Abs or S/A conjugated enzymes used in flow cytometry assays are provided in Table 3 herein below.

TABLE 3

| Reagent | Manufacture company | # |
|---|---|---|
| Avidin-Fluorescein (Avidin-FITC) | R&D Systems, Inc. | F0030 |
| APC Streptavidin | BD Biosciences. | 554067 |
| Alexa Fluor 647 goat anti mouse | Invitrogen | A31625 |
| Alexa Fluor 488 goat anti mouse | Invitrogen | A31620 |

Cell's labeling was detected using FACSCalibur (BD). Flow cytometry results were analyzed using FlowJo analysis software. Viable cells were defined by their FSC/SSC profiles and, in addition, their lack of 7AAD. Analysis of EpCAM subpopulations was performed by gating cell fractions according to EpCAM staining intensity (negative, dim or bright) versus FSC. The second marker was then examined in each subpopulation gate. When triple staining was performed, the EpCAM subpopulation was initially gated and then co-staining of the other two markers in each subpopulation was examined.

Results

SIX2:

Of the multiple regulatory genes specifying renal progenitors, SIX2 is a transcription factor that has been shown in mice to specify self-renewing epithelial renal stem cells that have the ability to give rise to all cell types in the nephron[6]. Immunostaining of mid-gestation human fetal kidney (FK) revealed localization of such SIX2-expressing cells to the metanephric mesenchyme (MM), specifically to the cap mesenchyme (CM), where renal stem cells are suggested to reside[6, 8] (FIGS. 1A, 1B). While unsuitable for human cell sorting, SIX2 staining highlights the location of the desired putative MM stem cells.

EpCAM (CD326).

Figure 2A:
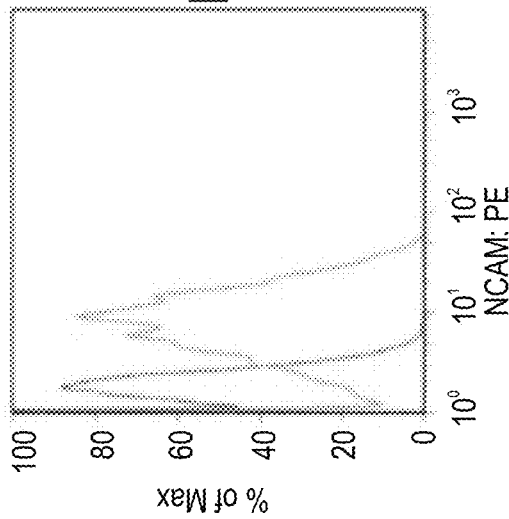
Figure 3A:
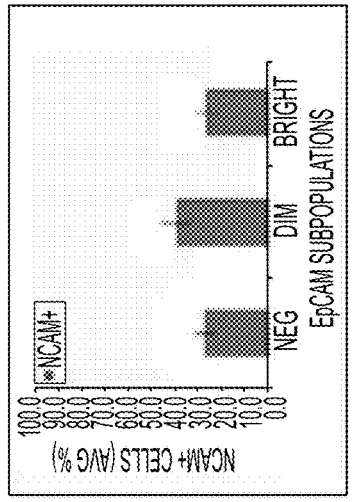
FIG. 3A is a representative zebra graph of EpCAM staining and the subpopulation gating. EpCAM subpopulations were gated according to EpCAM staining intensity (negative, dim or bright) versus FSC.
Figure 3B:
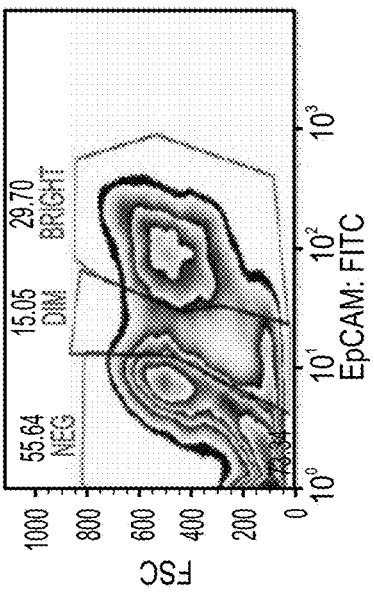
Figure 3E:
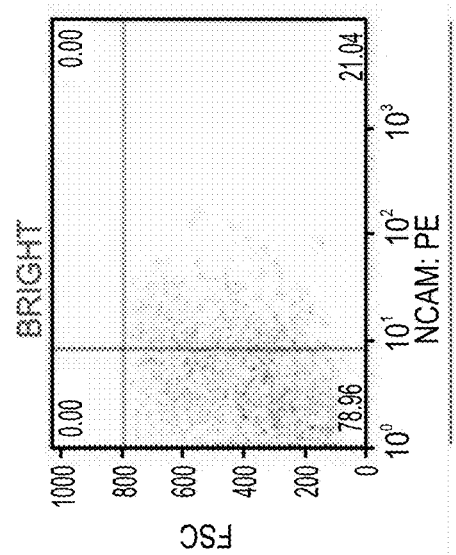
Figure 3C:
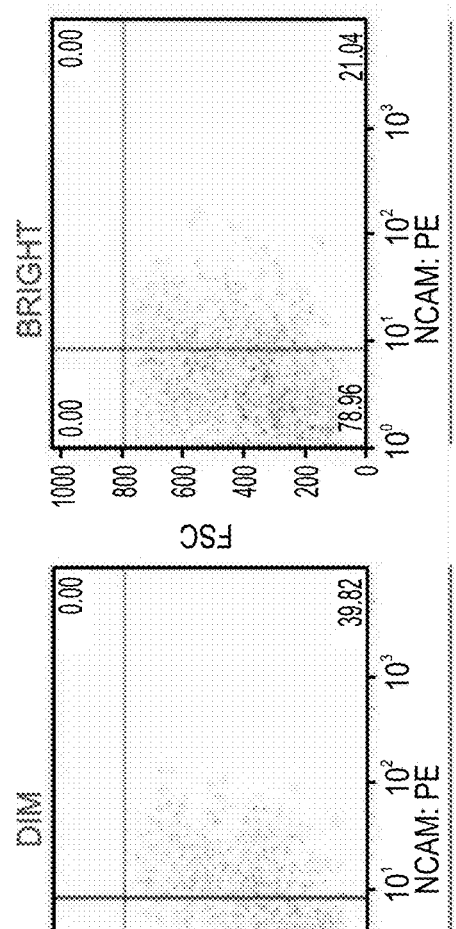
Figure 3D:
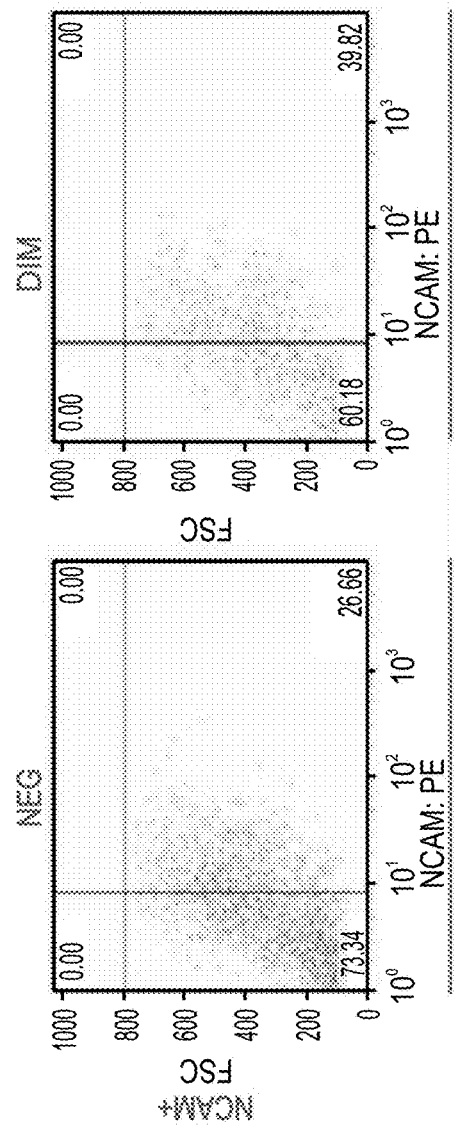

The Epithelial Cell Adhesion Molecule (EpCAM) is expressed virtually on all normal epithelia in vertebrates[22] and can therefore serve as a marker for epithelial differentiation. Accordingly, Trzpis et al[23] have recently shown that in mid-gestation human FK (by 10 weeks of gestation), hEpCAM was expressed by the ureteric bud (UB) and comma-shaped (C) and S-shaped (S) bodies, whereas the MM did not express hEpCAM. Moreover, they found differential hEpCAM staining levels during nephrogenesis, where the weakest staining for hEpCAM was observed in the comma- and S-shaped bodies, which are progenitor nephron derivatives of the MM and higher levels in the UB and developing tubules of the nephron, indicating a correlation between hEpCAM levels and the degree of epithelial differentiation. The present inventors examined cell populations of low-passage human FK cells by flow cytometry and revealed that 80.0±11.2% of the cells express EpCAM (FIG. 2A). This result correlated with its wide-spread distribution in epithelial cells of the developing kidney. Moreover two subpopulations within the EpCAM+ population, EpCAM$^{dim}$ and EpCAM$^{bright}$ were detected, suggestive of epithelial progenitor and more differentiated tubular cells, respectively (FIGS. 3A-Y). A clearer separation between EpCAM$^{dim}$ and EpCAM$^{bright}$ cell populations was noted in older HFK.

NCAM1 (CD56).

NCAM1 transcript levels were up-regulated in both human FK and stem-like WT xenografts (>three-fold increment)[16]. Immunostaining of sections of mid-gestation human FK (14-20 week) demonstrated predominant staining in the nephrogenic zone and renal stroma, while mature tubules were devoid of staining. In the nephrogenic zone, we observed strong expression in the CM, similar to SIX2 and also in early S and comma shaped nephron figures (i.e., MM and its derivatives) and newly forming tubules but not in UBs (FIGS. 1A-J). This staining pattern of NCAM1 has been observed in the developing mouse kidney[24, 25]. Examination of populations of low-passage human FK cells by single staining flow cytometry revealed that 29.1±8.2% of the cells express NCAM1 (FIG. 2B), representing nephrogenic zone and stroma-derived NCAM expressing cells. Two sub-populations of NCAM cells, NCAM$^+$EpCAM$^-$ (13.5±4.9% of total cells) and NCAM$^+$EpCAM$^+$ (14.5±3.7% of total cells) were also detected. Because EpCAM is not expressed in the stroma or in the MM, the NCAM$^+$EpCAM$^-$ subpopulation is indicative of cells originating from both of these areas, while NCAM$^+$EpCAM$^+$ cells are a heterogeneous pool of progenitor cells from the nephrogenic zone, including newly developed tubules. This sub-population could be further separated into NCAM$^+$EpCAM$^{dim}$ and NCAM$^+$EpCAM$^{bright}$ cell fractions ((FIGS. 3B-E)). In the EpCAM$^{dim}$ population a significantly larger fraction consists of NCAM expressing cells compared to that found in the EpCAM$^{bright}$ cell fraction (P<0.0001) (FIGS. 3B-E), further indicating NCAM as an epithelial progenitor marker. Taking into account that in the nephrogenic zone low levels of EpCAM were previously noted in the immediate MM-derived structures (S- and comma-shaped) and higher levels in emerging tubules, the NCAM$^+$EpCAM$^{dim}$ cells possibly represent the former. In addition, the present inventors have analyzed the long chain form of polysialic acid (PSA) characteristic of the low adhesive embryonic form of NCAM (PSA-NCAM), the probe of which was not included in the microarrays[16]. This surface marker closely resembles NCAM's staining pattern (various developmental stages including condensed MM, renal vesicles, the distal portion of S-shaped bodies, and primitive tubules) but is not detected in the renal stroma. Accordingly, PSA-NCAM was found to be expressed in 8.6±3.2% of HFK cells (FIG. 2E) and to peak in the EpCAM$^{dim}$ cell fraction (P<0.015 compared to the EpCAM$^{bright}$ cell fraction) (FIGS. 3F-I). Furthermore, PSA$^+$EpCAM$^-$ and PSA$^+$EpCAM$^+$ cell fractions are more limited in expression by comparison to NCAM/EpCAM (2.3±1.3% and 4.2±0.9% of total cells, respectively). Interestingly, when applying triple staining for PSA, NCAM and EpCAM the putative MM cell fraction, NCAM$^+$PSA$^+$EpCAM$^-$ was found to be expressed in 2.5±2.2% of total cells, while NCAM$^+$PSA$^+$EpCAM$^+$ from later developmental stages in 4.3±0.3% of total cells (FIGS. 4C-D), indicating that PSA and NCAM localize in similar progenitor areas. NCAM$^-$PSA$^+$EpCAM$^-$ cells could not be detected.

Frizzled 2,7 (FZD2, FZD7).

Figures 1E, 1F:
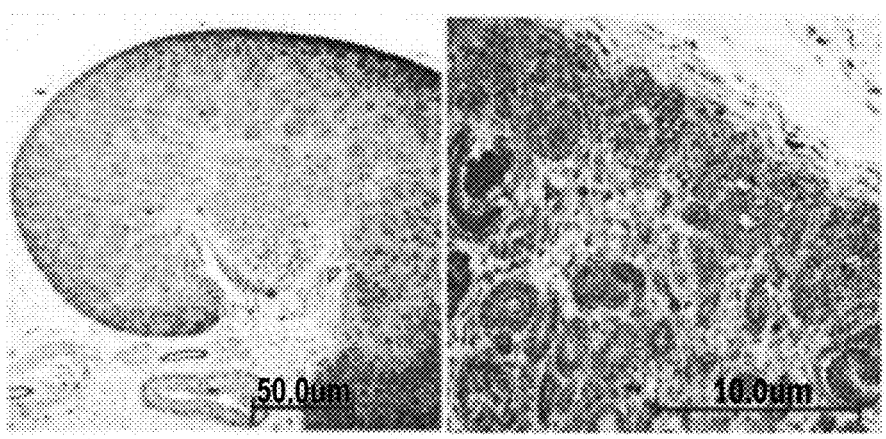
Figure 2B:
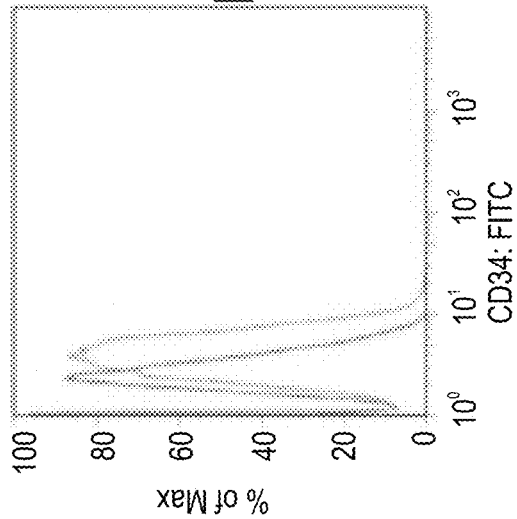

Both transcript levels of FZD2 and FZD7 (Wnt receptors) were up-regulated in both human FK and stem-like WT xenografts[16]. Recently, activation of the Wnt/β-catenin pathway has been shown to maintain the progenitor pool in the metanephric mesenchyme[27]. Thus, FZDs represent surface marker molecules that may have a functional role in maintaining progenitor cells. Immunostaining of sections of mid-gestation human FK (14-20 week) revealed that while FZD2 demonstrated widespread expression (FIGS. 5A-L), staining all of the tubular cells, FZD7 was detected predominantly in the nephrogenic zone, staining all cell types in that area [MM (both loose and condensed mesenchyme), UBs, early nephron figures, newly forming tubules] but not at all in renal stroma (FIGS. 1E-F). Correlating with its reserved localization, FZD7 was detected in only 9.5±3.7% of the HFK cells (FIG. 2F). Examination of the FZD7 expressing cells in relation with EpCAM sub-populations showed that largest fractions of FZD7$^+$ cells exists within the EpCAM$^{neg}$ and EpCAM$^{dim}$ fraction and to a much lesser extent in the EpCAM$^{bright}$ cell fraction (P<0.02) (FIGS. 3J-L). Thus, while EpCAM$^+$FZD7$^-$ cells represent the largest fraction (53.8±13.4% of total cells), FZD7$^+$EpCAM$^+$ cells were observed (3.9±1.2% of total cells) which likely represent MM- and UB-derived progenitors and FZD7$^+$EpCAM$^-$ cells (2.5±0.6% of total cells), which may originate solely from the MM. Furthermore, using triple FACS staining of HFK cells that also includes NCAM (FIGS. 4G-H) the present inventors were able to demonstrate cell populations of the FZD7$^+$EpCAM$^+$NCAM$^+$ progenitor phenotype (MM-derived, 2.5±1.0% of total cells, 4.7±1.0% FZD7$^+$NCAM$^+$ cells within the EpCAM population) as well as FZD7$^+$NCAM$^+$EpCAM$^-$ (0.6±0.5% of total cells, 2.2±0.7% FZD7$^+$NCAM$^+$ cells within the EpCAM$^-$ population) and surprisingly also FZD7$^+$EpCAM$^-$NCAM$^-$ phenotypes (2.0±0.8% of total cells, 7.8±4.18% FZD7$^+$NCAM$^-$ cells within the EpCAM population), which are both likely to represent putative MM-originating stem cells.

Activin Receptor IIB (ACVRIIB).

Figure 1G:
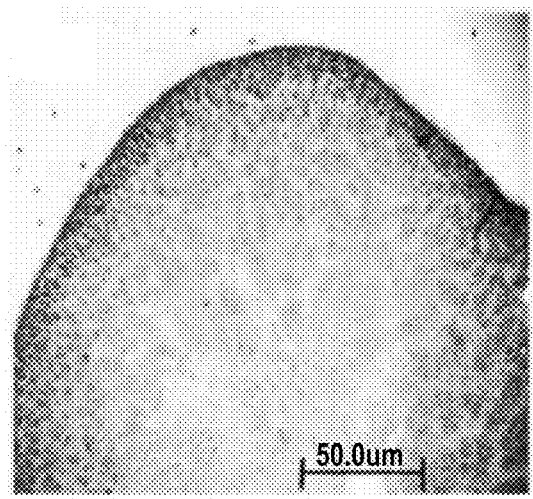
Figure 1H:
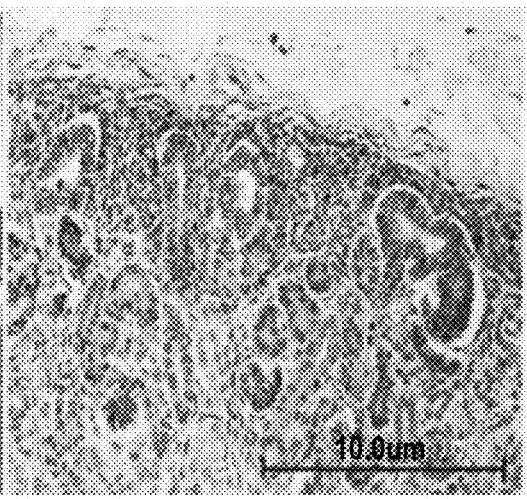

ACVRIIB qualified as a microarray predicted marker. Interestingly, mice lacking ACVRIIB show abnormalities in kidney development and in anterior/posterior patterning of the axial skeleton show abnormalities[28, 29], further emphasizing functional importance in the renal progenitor population. Similar to NCAM and FZD7, in the sections of human FK, ACVRIIB was preferentially localized to the nephrogenic zone, showing strong expression in all structure types (blastema, UBs, comma- and S-shaped bodies and also developing tubules). ACVRIIB was also detected in parietal epithelium of fetal glomeruli but not on stromal cells (FIGS. 1G-H). A similar staining pattern was observed by in-situ hybridization of E14.5 mouse kidneys (robust expression of ActRIIB mRNA in the condensed metanephric mesenchyme, differentiating nephrons and UB branches). While according to its localization ACVRIIB has potential as a renal progenitor marker, FACS analysis of HFK cells showed extremely varying expression levels and precluded its further investigation.

NTRK2.

Figure 1I:
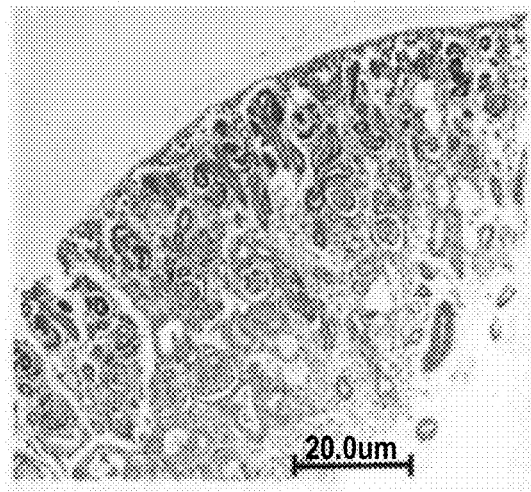
Figure 1J:
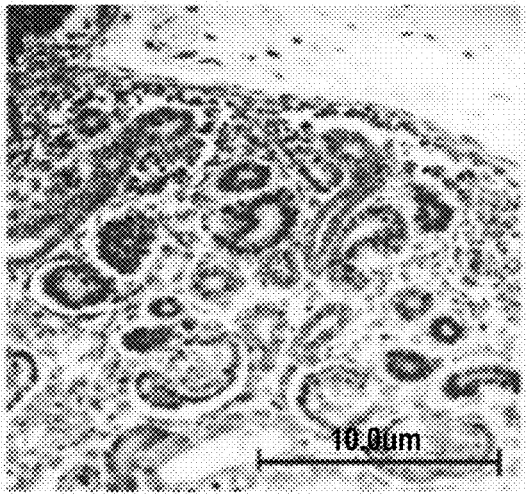
Figure 2C:
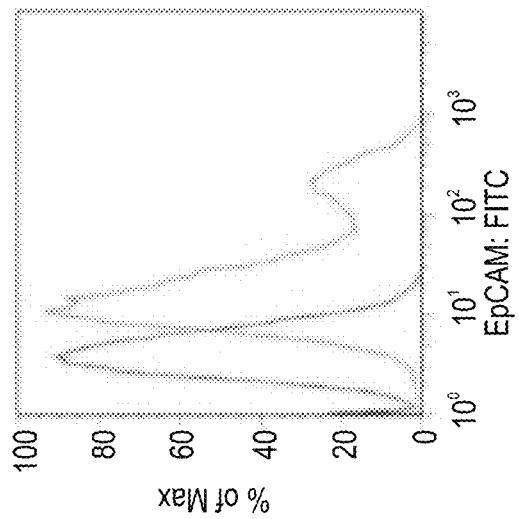
Figure 2D:
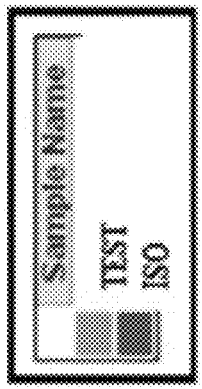
Figure 4B:
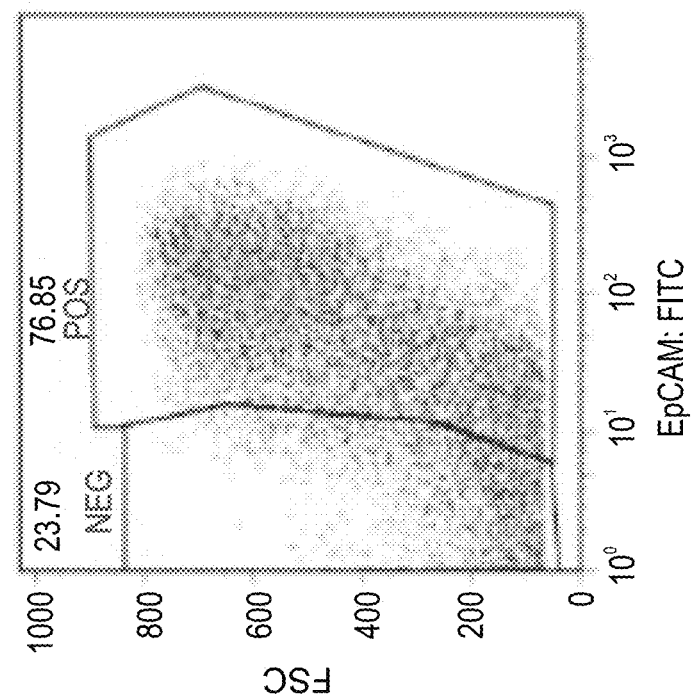
FIGS. 4A-B are representative dot plot graphs of EpCAM staining. Cells were gated in two groups: EpCAM negative (neg) and EpCAM positive (pos) versus FSC.
Figure 4A:
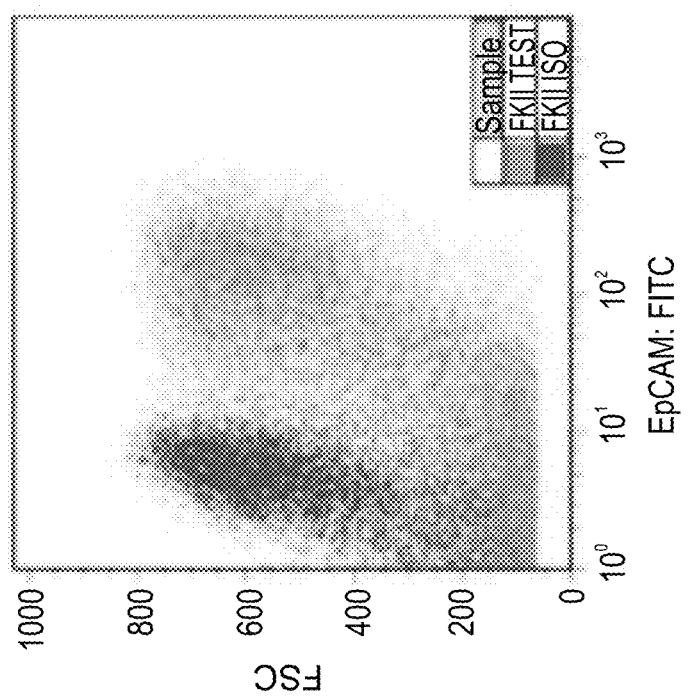

NTRK2 qualified as a microarray predicted marker as similar to FZD7 it was up-regulated in microarrays of WT-stem like tumors and human FK. Previous analysis of the developing mouse kidney showed NTRK2 to localize to the MM while in WT NTRK2 has been suggested as a bad prognostic marker[30]. Immunostaining of the human FK showed NTRK2 to localize to cells within the MM but also to early differentiation stages in the nephrogenic zone and some differentiated tubules but not stroma (FIGS. 1I-J). FACS analysis revealed NTRK2 to stain 12.1±3.4% of the human FK (FIG. 2C). Analysis of NTRK2 according to EpCAM subpopulations revealed a tendency towards higher expression levels in both the negative and dim fraction compared to the bright one (FIGS. 3N-Q). To further strengthen the presence of progenitor phenotypes the present inventors found by triple staining of NTRK2 along with NCAM and EpCAM, EpCAM$^+$NCAM$^+$NTRK2$^+$ cells (3.1±2.5% of total, 6.8±3.3% NCAM$^+$NTRK2$^+$ cells within the EpCAM$^+$ population) as well as putative MM stem cell populations, EpCAMNCAM$^+$NTRK2$^+$ cells (0.61±0.3% of total, 3.3±2.5% NCAM$^+$NTRK2$^+$ cells within the EpCAM$^-$ population) and EpCAM$^-$NCAM$^-$ NTRK2$^+$ cells (2.7±2.4% of total, 7.5±2.7% NCAM$^-$NTRK2$^+$ cells within the EpCAM$^-$ population) (FIGS. 4K-L).

GPR39, DLK1.

Figures 5A, 5B:
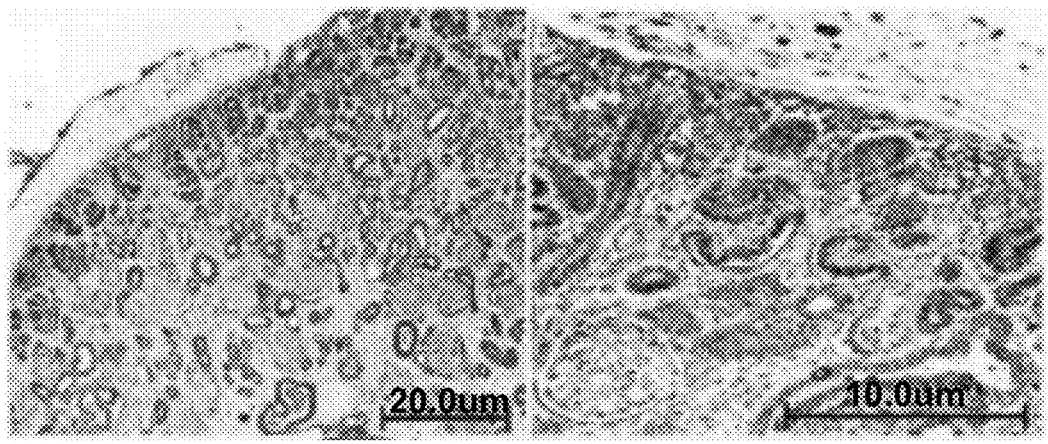
FIGS. 5A-L are photographs illustrating immunostaining of FZD2, GPR39, DLK1, CD34, CD90 and CD24 in paraffin embedded sections of HFK (12 or 19 weeks of gestation); (A-B) FZD2 immunostaining demonstrates widespread staining of renal tubules. (C-D) GPR39 immunostaining demonstrates ubiquitous expression in differentiated renal tubular and to a lesser extent in componenets of the nephrogenic cortex. (E-F) Dlk1 immunostaining demonstrates ubiquitous expression in differentiated renal tubular but not in MM and its derivatives renal, UBs or stroma. (G-H) CD34 immunostaining demonstrates exclusive localization to endothelial cells (glomerular and peri-tubular) in all parts of the HFK, including in the nephrogenic cortex. (I-J) CD90 immunostaining demonstrates predominant staining in renal tubular cells but not in MM and its derivatives, UBs or stroma. (K-L) CD24 immunostaining demonstrates widespread expression in mature tubules. Figure (C) is shown in low magnification (original ×4), Figures A, E, G, I, K and B, D, F, H, J and L are shown in higher magnifications (original ×20 and ×40, respectively).
Figures 5C, 5D:
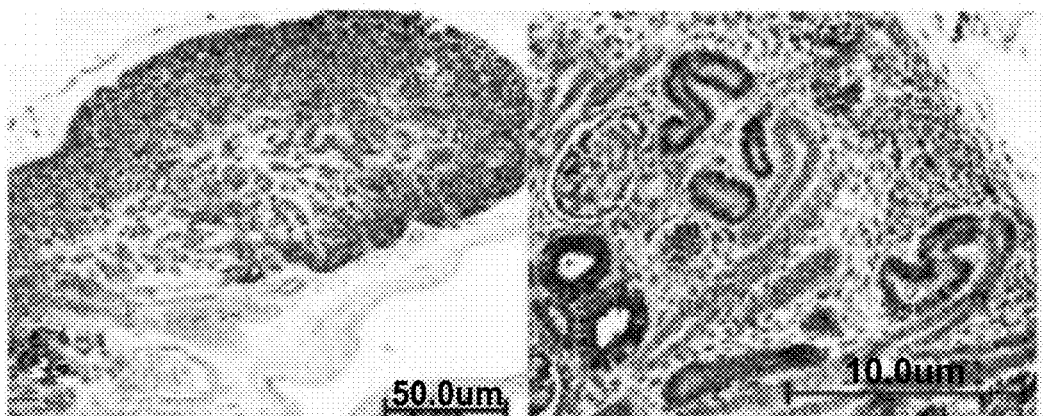
Figures 5E, 5F:
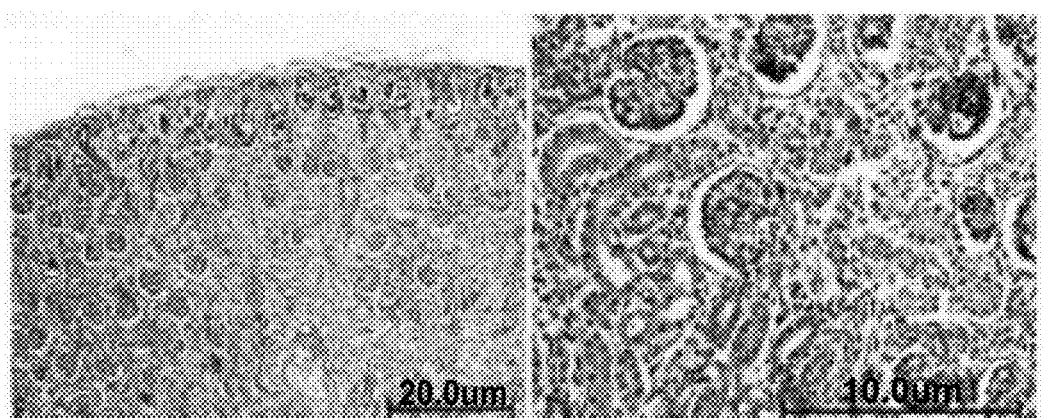
Figures 5G, 5H:
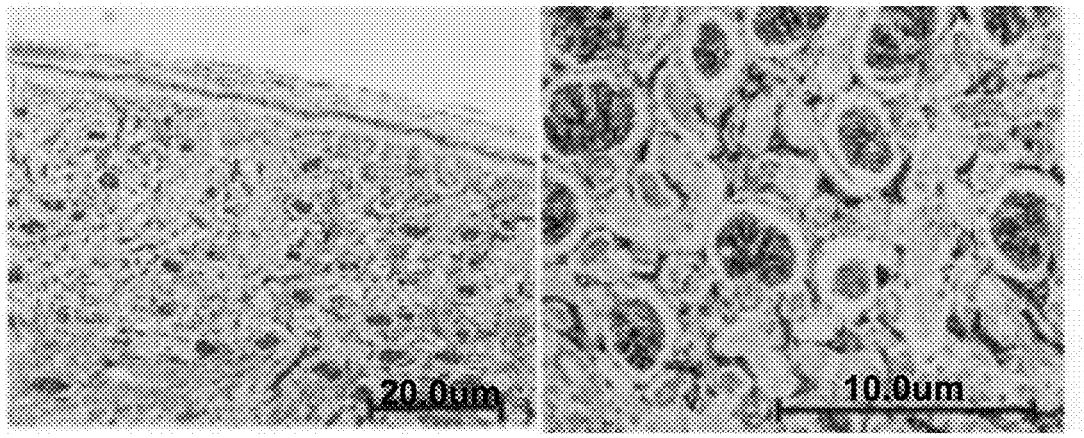
Figures 5I, 5J:
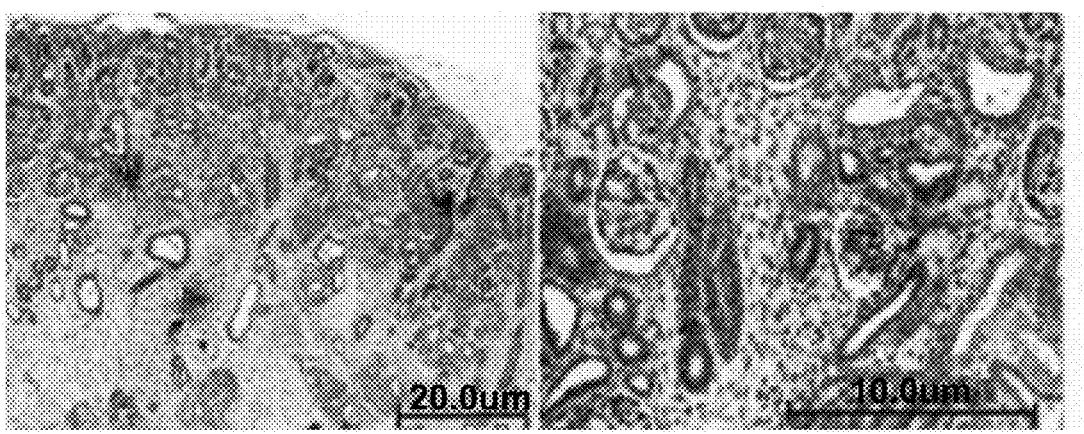

These markers, up-regulated in microarrays of both human FK and stem-like WT xenografts, were found to be ubiquitously expressed in differentiated renal tubular epithelial cells in sections of human FK while only faintly positive or negative in progenitor structures of the nephrogenic zone and were therefore eliminated from FACS analysis (FIG. 5C-D).

CD34.

CD34 is a well known marker of hematopoietic stem cells (HSC)[31]. FACS analysis demonstrated CD34 to be expressed in 14.4±12.9% of HFK cells. Immunostaining for the CD34 protein specifically demonstrated widespread endothelial localization (glomerular and peri-tubular) in all parts of the human FK (FIG. 5G-H), including in the nephrogenic zone whereas CM and other epithelial progenitor structures are devoid of CD34 expression. CD34 is therefore not an epithelial stem cell marker in the human FK but rather a marker for vascular differentiation. c-Kit, an additional hematopoietic stem cell marker, was not detected in the human FK cells.

CD90.

Antigenic phenotypes of adult MSC consistently include CD90 and CD105[32]. In addition, CD90 was shown to be broadly expressed on heterogeneous rat fetal kidney cells transplanted to injured kidneys[13]. Immunolocalization of CD90 in the human FK revealed predominant expression in renal tubular cells but not in the nephrogenic zone (FIGS. 5I-J) and 25.3±8.5% of HFK cells expressed CD90.

CD24.

Figures 5K, 5L:
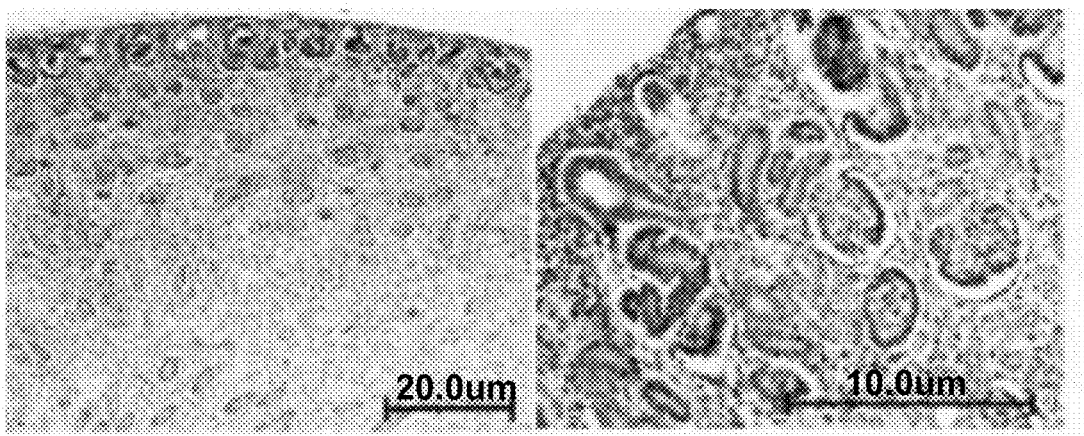

CD24 was not differentially expressed in the developing human kidneys or in WT stem-like xenografts. Nevertheless, the previous demonstration of CD24 as characteristic of the molecular phenotype of renal progenitor cells in the developing mouse kidneys[33], as well as the utilization of CD24 (along with CD133) to specify human renal progenitor cells[34] from developing human kidneys, led the present inventors to examine its expression Immunostaining of human FK showed widespread expression and localized CD24 to mature tubules (renal stroma was devoid of CD24) (FIGS. 5K-L). Accordingly, FACS analysis demonstrated that approximately 73.6±20.6% of HFK cells express CD24 (FIG. 2H). When analyzed in regard with EpCAM subpopulations, the abundance of CD24 expressing cells increases along epithelial differentiation (in contrast with for instance FZD7) so that approximately 80% of the EpCAM$^{bright}$ cells are CD24$^+$ cells (P<0.0001 compared to CD24$^+$ cells found in the dim and negative fractions) (FIG. 3R-U), indicating that CD24 is predominantly a marker of differentiation in the human FK. Moreover, triple staining with NCAM revealed that CD24 is expressed in low levels only in putative MM fractions; CD24$^+$NCAM$^+$EpCAM$^-$ and CD24$^+$NCAM$^-$EpCAM$^-$ cell fractions (2.0±1.2%, 3.7±2.8% of total cells, respectively) in contrast to a CD24$^+$NCAM$^-$EpCAM$^+$ differentiated phenotype (34.1±14.6% of total cells) (FIGS. 4E-F). Thus, sorting cells from the human FK according to CD24 would result in a heterogeneous population comprised predominantly of differentiated cells and to a much lesser extent of stem/progenitor cells.

CD133.

Figure 2I:
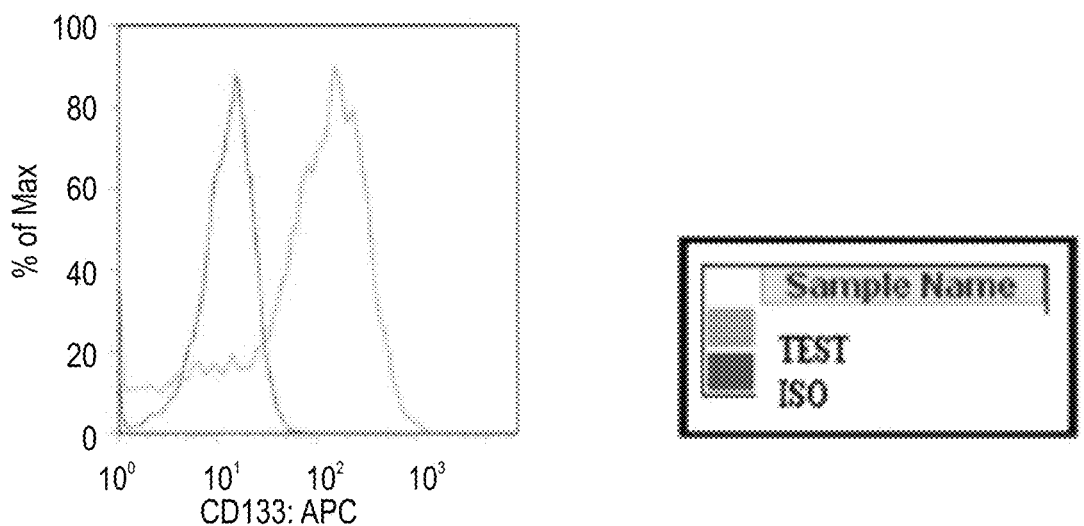
Figure 2J:
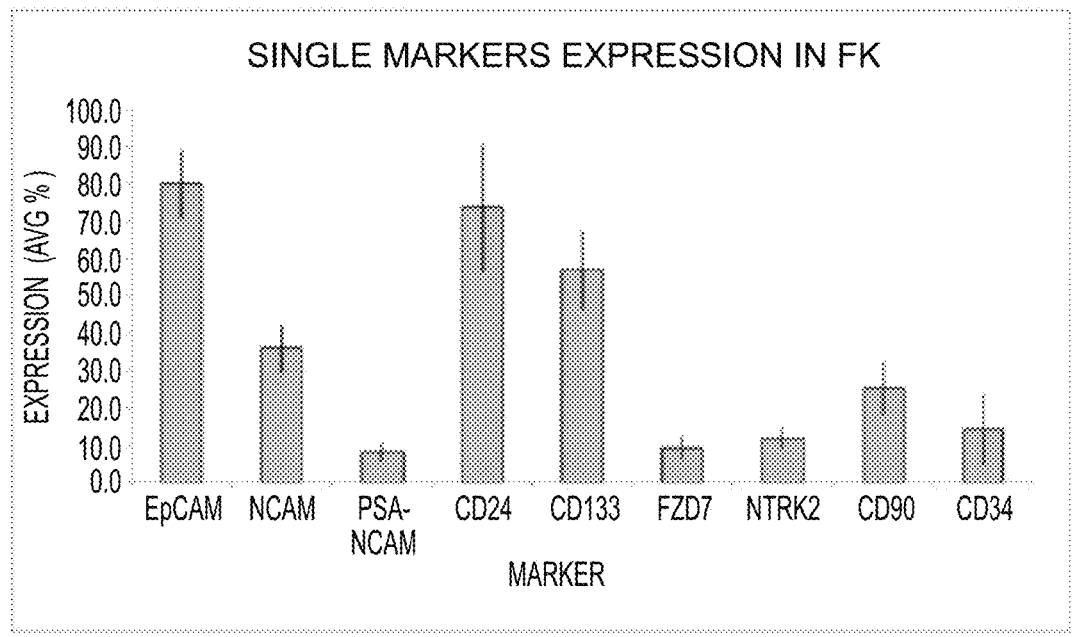
FIG. 2J is a summarizing bar graph of single marker staining in HFK (17-21 weeks of gestation). Data were calculated as average % of expressing cell±SD. Each marker was tested in 10 HFK.

Although the biological function of CD133 remains unknown, CD133 is recognized as a stem cell marker for normal and cancerous tissues[35]. Indeed, CD133 alone or in a combination with other markers is currently used for the isolation of stem cells from numerous tissues, such as bone marrow, brain, prostate, liver, pancreas[35-38], and both developing and adult kidney (along with CD24)[34, 39]. Among adult organs, the kidney has been reported to have large numbers of CD133$^+$ cells[35, 40]. As previously shown for the fetal pancreas, detect CD133 positively in human fetal kidney tissue could not be detected. However, FACS analysis of human FK cells demonstrated that 56.9±15.8% of the cells express CD133 (FIG. 2I). Furthermore, the EpCAM$^{bright}$ fraction contained the largest population of CD133 expressing cells with significantly smaller populations in EpCAM$^{dim}$ and EpCAM$^{neg}$ cells (P<0.0001) (FIGS. 3V-Y). In addition, similar to CD24, triple FACS staining demonstrated a large population of CD133$^+$EpCAM$^+$NCAM$^-$ cells (29.5±10.6% of total cells) and a relatively small ones of the CD133$^+$NCAM$^+$EpCAM$^+$ (14.4±4.5% of total cells) and CD133$^+$NCAM$^+$EpCAM$^-$ putative progenitor and stem phenotypes (1.1±1.2% of total cells) (FIGS. 4I-J). Because CD24$^+$CD133$^+$ cells have been recently suggested a renal 'stem cell' fraction[34], the present inventors analyzed expression of CD133 in conjunction with CD24. Double staining showed that the CD24$^+$CD133$^+$ fraction comprises 55.5±6.4% of the human FK cells, while triple staining with EpCAM showed that within the EpCAM$^{bright}$ fraction approximately 60% of the cells are CD24$^+$CD133$^+$ and to a much lesser extent in the EpCAM$^{dim}$ and EpCAM$^{neg}$ cell fractions (P<0.0001) (FIGS. 4I-J). Thus, similar to cells expressing the CD24 marker, most of the CD133$^+$ cells in the human FK and also CD133$^+$CD24$^+$ cells are of a differentiated tubular phenotype and are not in any way exclusive to the stem/progenitor pool.

Marker Expression in the Human Adult Kidney.

Figure 6A:
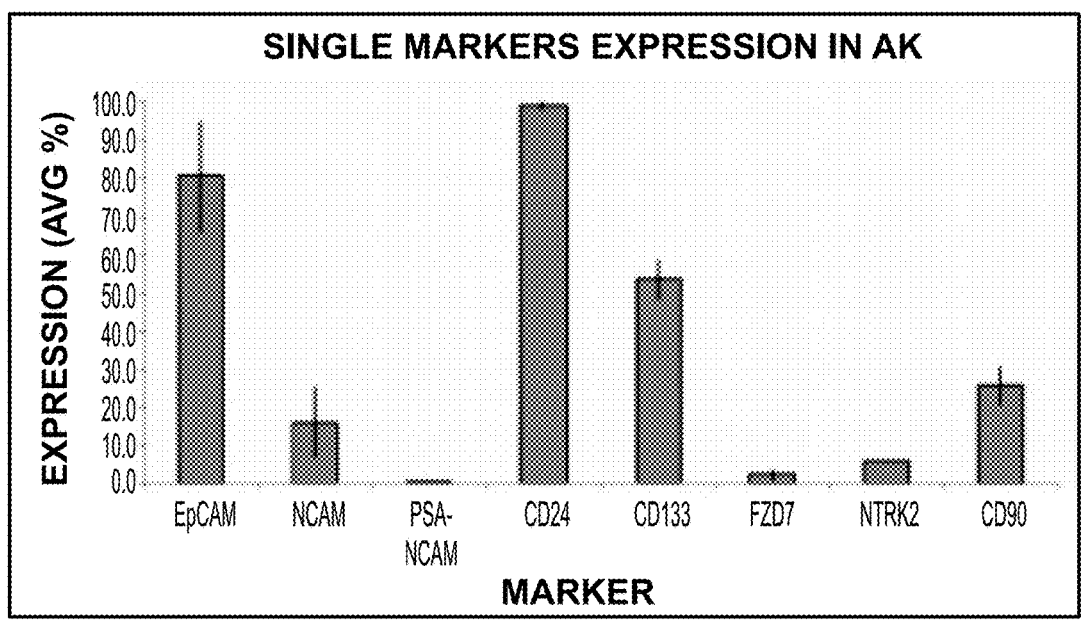
FIG. 6A is a summarizing bar graph of single marker staining in human adult kidneys (HAK). Data were calculated as average % of expressing cell±SD. Each marker was tested in 3 HAK.
Figure 6B:
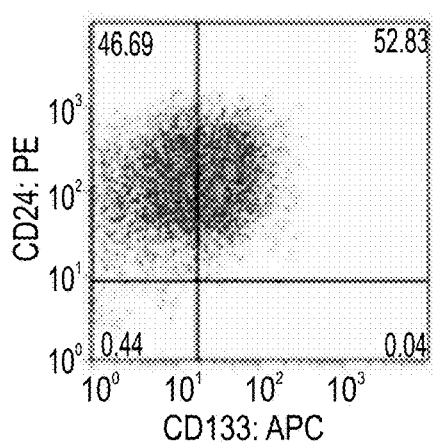
FIG. 6B is a representative dot plot graph of CD24 and CD133 co-staining demonstrating a large fraction of CD24$^+$CD133$^+$ cells in HAK. Quadrates were placed according to the isotype control confiding the negative staining to the lower left quadrant. Percentage of cells for each marker combination appears in the quadrant.

Renal cell progenitor markers are expected to decrease once maturation occurs. The present inventors therefore analyzed cell surface marker expression in the human adult kidney (HAK). FACS analysis of HAK cells for single marker expression revealed reduced PSA-NCAM, FZD7, NTRK2 and NCAM levels compared to HFK, indicative of a progenitor origin (FIGS. 6A-B). In contrast, similar and even increased expression levels in the HAK were observed for CD105, CD90, CD133 and CD24 (FIGS. 6A-B). Moreover, CD24$^+$CD133$^+$ cells represent a large cell fraction in the HAK, comprising 64.26±10.15% of the total cells.

Discussion

In the present example, the present inventor has analyzed for the expression of putative stem cell markers in the human fetal kidney. Using comprehensive immunocytochemical and flow cytometric analysis of human FK cells, the expression profile of a variety of surface antigens were characterized, some of which are considered markers of organ-specific stem cells and the others have been recently suggested to appear on malignant renal stem/progenitor cells of wilms' tumors and in human FK[16]. Given the similarities in molecular marker expression in progenitors from wilms' tumors and the developing human kidney, it appears likely that these cell populations are derivatives of the same lineage.

Figure 7:
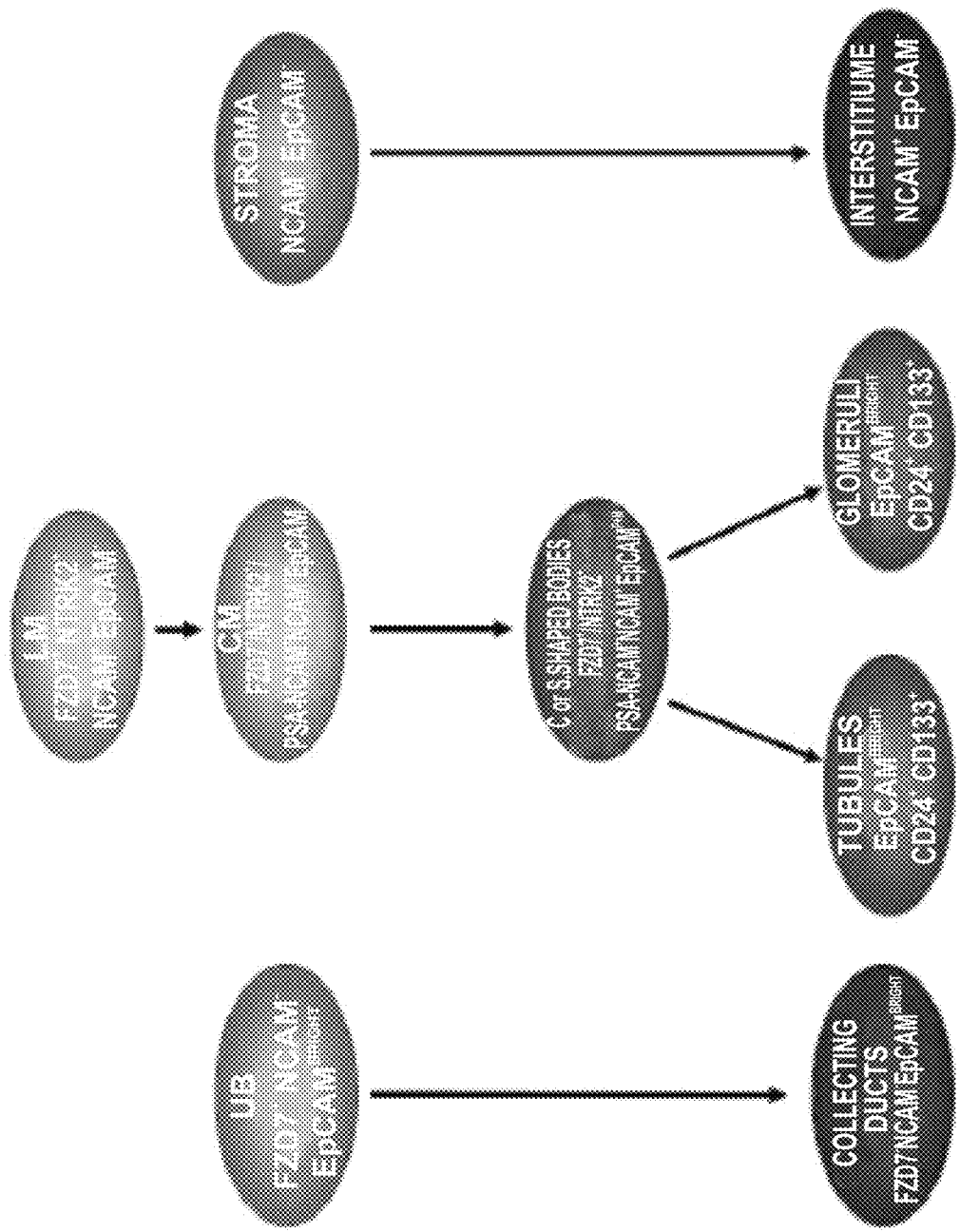
FIG. 7 is a hypothetical model of regional identity of human fetal kidney cells according to changes in surface marker expression during differentiation of the nephric-lineage. Note that CD24 or CD133 can be also added as a third marker to NCAM$^+$EpCAM$^-$ NCAM$^+$EpCAM$^+$ populations and as such represent putative stem/progenitor cell populations. Abbreviations: MM, metanephric mesenchyme; CM, condensed mesenchyme; LM, loose mesenchyme; UB, ureteric bud.

The present data suggest that none of these putative stem cell markers are restricted to kidney-specific epithelial stem/progenitor cells, but on the contrary, stem cell markers are always also expressed on differentiated elements. The necessity for marker combination is shown not only by lack of specific staining of the nephrogenic mesenchyme but also by high percentage of expression of single markers in human FK cells, over 50% of cells for markers such as CD24 and CD133, as well as the relative high marker abundance within the EpCAM$^{bright}$ fraction. Because CD24 and CD133 mostly qualify as markers for identification of differentiated tubular cells, their combination will not enrich for a progenitor phenotype. More relevant for the enrichment of stem/progenitor cells is the utilization in combination of at least one of the markers that were found to localize predominantly to the nephrogenic zone and to a much lesser extent to differentiated epithelia (NCAM, PSA-NCAM, FZD7, and NTRK2). Interestingly, using a highly reliable antibody the present inventors have recently identified NCAM as a candidate marker for the renal malignant progenitor population of wilms' tumor[41]. Because NCAM is not at all expressed on UBs or differentiated epithelia it can be extremely useful for positive selection of MM-derived progenitor nephron populations (NCAM$^+$X$^+$) if the second marker is clearly not detected on MM and stromal cells. This definition is most suitable for the NCAM$^+$EpCAM$^+$ fraction which was detected among the human FK cells. Moreover, because EpCAM is differentially expressed in the nephrogenic zone[23], identification of the NCAM$^+$EpCAM$^{dim}$ subset, possibly pinpoints an earlier MM-derived progenitor population (FIG. 7). Second markers that are expressed in all parts of the nephrogenic zone and are not detected on stromal cells potentially produce populations that include both MM-stem cells and a heterogeneous MM-derived progenitor population of the nephrogenic zone. This includes a wide variety of second marker combination, such as the rather small and discrete populations of NCAM$^+$FZD7$^+$ or NCAM$^+$NTRK2$^+$ cells which were identified, but potentially also larger NCAM$^+$CD24$^+$ and NCAM$^+$CD133$^+$ cell populations (if indeed CD133 will be directly shown not to localize to stromal cells).

The rarities of putative MM-stem cells arising from condensates is demonstrated by triple FACS staining of these cell populations with EpCAM and analysis for those populations that totally lack epithelial differentiation (EpCAM$^{neg}$). In all cases these were the smallest populations by comparison to EpCAM expressing fraction, showing NCAM$^+$FZD7$^+$EpCAM$^-$, NCAM$^+$NTRK2$^+$EpCAM$^-$ and NCAM$^+$CD133$^+$EpCAM$^-$ cell fractions to be ≤1% of HFK cells, and NCAM$^+$PSA$^+$EpCAM$^-$~2.5% of the cells. Interestingly, within the EpCAM$^{neg}$ fraction there were NCAM$^-$FZD7$^+$ or NCAM NTRK2$^+$ but not NCAM$^-$PSA$^+$ cells. These findings correlate with staining patterns in which FZD7 and NTRK2 also localize to loose mesenchyme (LM) while PSA appears with condensation, possibly indicating the former fractions to arise from LM (FIG. 7).

In practice, cell sorting according to two positive markers and one negative is likely to be cumbersome and therefore eliminating EpCAM after positively selecting for a single marker that is expressed exclusively along the developmental stages of renal epithelia (MM, MM/UB-derived progenitors, developing and developed tubules but not stroma) might be more practical for sorting MM-enriched stem cells. In this setting, using an initial marker that localizes preferentially to the nephrogenic zone as opposed to a predominantly marker of differentiation is advantageous. One such potential combination includes the very small but consistent population of FZD7$^+$EpCAM$^-$ or PSA$^+$EpCAM$^-$ cells. In any event, the relative paucity of stem/progenitor phenotypes highlights the need for early sorting of human FK cells according to marker molecules followed by their expansion in vitro rater than application of multipassage culture of unsorted heterogeneous human FK cells for cell selection[42].

The profiling of renal surface antigens initiated here forms the basis for exploring other markers and for investigating the function of suggested progenitor cell sub-populations in the renal context (FIG. 7).

Example 2

HFK Cell Sub Populations Sorted According to Specific Markers Retain in Culture Molecular Aspects of Regional Identity and Stemness Profile Because immunostaining of HFK demonstrated that the markers are regionally specified, the present inventor wanted to verify that regional differences are maintained in HFK cells. As a proof-of-principle sorted NCAM$^+$EpCAM$^-$, NCAM$^+$EpCAM$^+$ (containing putative MM stem- and MM-derived progenitor cells, respectively) were compared with NCAM$^-$ HFK cell populations as NCAM and EpCAM are important surface markers for the present characterization system.

Materials and Methods

Magnetic Cell Sorting:

At least three independent kidney samples were used for sorting of NCAM/EpCAM as well as PSA-NCAM subpopulations. Sorted cells were of primary cultures established from the same HFK used in the FACS analysis of progenitor marker expression. Cells were detached with Trypsin/EDTA and resuspended in growth medium. Cells were transferred trough 30 µm Pre-Separation Filter (Miltenyi Biotec GmbH, Bergisch Gladbach, Germany) then washed and resuspended in pH 7.2 MACS buffer (0.5% BSA, 2 mM EDTA in PBSX1). Cells were magnetically labeled with NCAM1 (CD56) MultiSort MicroBeads kit (Miltenyi Biotec GmbH) according to the manufacturers instructions and positive labeled cells (NCAM$^+$) were enriched with LS Columns CD56 MicroBeads were released from the cells with MultiSort Release Reagent (Miltenyi Biotec GmbH) and CD56 positive cells were further separated with EpCAM (CD326) positive and negative cells using CD326 MicroBeads (Miltenyi Biotec GmbH) on LS Columns according to the manufacturer's instructions. Enrichment of cells to CD56 and CD326 was validated using flow cytometry.

Quantitative Reverse Transcription-PCR:

Sorted NCAM$^+$EpCAM$^-$, NCAM$^+$EpCAM$^+$ and NCAM sub-populations of HFK were tested for the expression of:

1. Transcription factors specifying renal stem/progenitor cells in the MM (SIX2, CITED1, SALL1, WT1, PAX2) (Cho E A, Dressler G R. San Diego: San Diego: Academic Press; 2003. In The Kidney: From Normal Development to Congenital Disease. pp. 195-210; Cicero S A, et al. Proc Natl Acad Sci USA. 2009; 106(16):6685-6690);

2. The marker pair Vimentin/E-cadherin that are expressed in early stages of kidney development during mesenchymal (Vim+) to epithelial (E-cad+) conversion and differentiation (Cho E A, Dressler G R. San Diego: San Diego: Academic Press; 2003. In The Kidney: From Normal Development to Congenital Disease. pp. 195-210; Cicero S A, et al. Proc Natl Acad Sci USA. 2009; 106(16):6685-6690).

3. 'Stemness' genes (Wnt pathway, β-catenin; Polycomb group, EZH2, BMI1) 4. Pluripotency genes (NANOG, OCT4) and 5. Surface markers (ACR2B, FZD7, NTRK2, CD133 and CD24). In addition, sorted PSA-NCAM$^+$ and PSA-NCAM$^-$ HFK cells were analyzed for the expression of genes included in groups 1 and 2. Total RNA from cells was isolated using RNeasy Micro Kit (Qiagen GmbH, Hilden, Germany) according to the manufacturer's instructions. cDNA was synthesized using High Capacity cDNA Reverse Transcription kit (Applied Biosystems, California USA) on total RNA. Real-time PCR was performed using an ABI7900HT sequence detection system (Perkin-Elmer/Applied Biosystems) in the presence of TaqMan Gene Expression Master Mix (Applied Biosystems). PCR amplification was performed using gene specific TaqMan Gene Expression Assay-Pre-Made kits (Applied Biosystems). PCR results were analyzed using SDS RQ Manager 1.2 software. Statistical analysis was performed using a non-paired 2-tails T-test. Statistical significance was considered at $P<0.05$.

Results

Figure 9A:
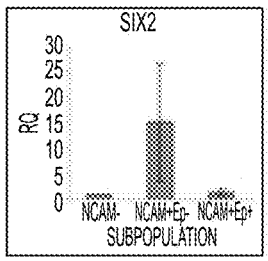
FIGS. 9A-Q are graphs illustrating gene expression analysis in sorted NCAM/EpCAM subpopulations. Quantitative reverse transcription-polymerase chain reaction (qRT-PCR) analysis of (A-E) renal stem/progenitor genes (Six2, Cited1, Sall1, Wt1 and Pax2), (F-G) vimentin and E-cadherin (H-L) 'sternness' genes (β-catenin/CTNNB1, EZH2, BMI1, Nanog and Oct4) and (M-Q) surface marker (FZD7, ACR2B, NTRK2, CD24 and CD133) gene expression in NCAM/EpCAM magnetically separated cells from HFK (15-19 weeks of gestation). Normalization was performed against control HPRT expression and RQ calculated relative to the NCAM− fraction. Data were calculated as average±SD of at least 3 independent samples. ***P<0.001, *P<0.05 versus NCAM−. Sall1 expression in NCAM$^+$Ep-CAM$^+$ cells was near significance (p<0.059).
Figure 9F:
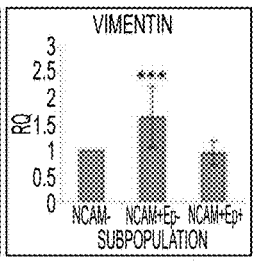
Figure 9H:
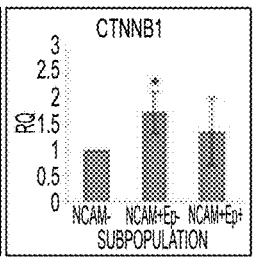
Figure 9M:
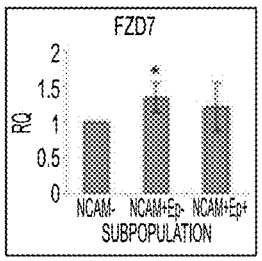
Figure 9B:
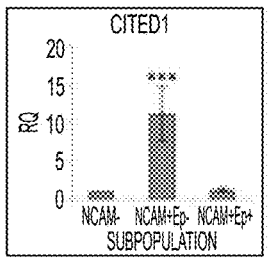
Figure 9G:
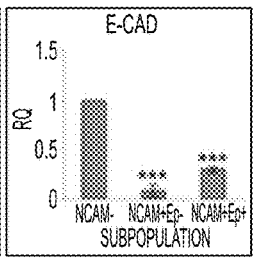
Figure 9I:
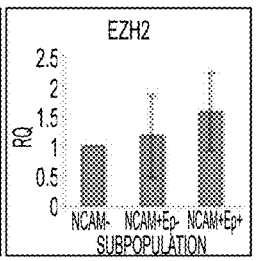
Figure 9N:
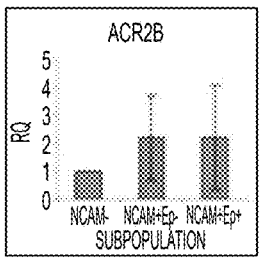
Figure 9C:
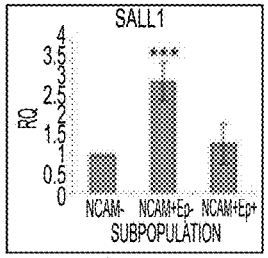
Figure 9J:
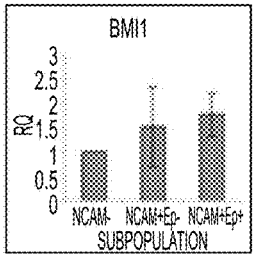
Figure 9O:
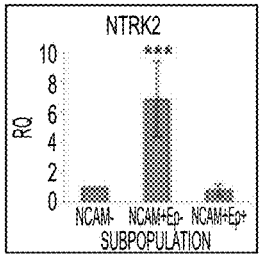
Figure 9D:
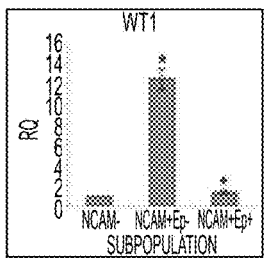
Figure 9K:
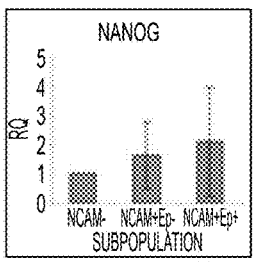
Figure 9P:
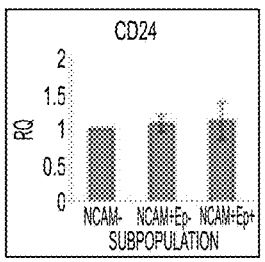
Figure 9E:
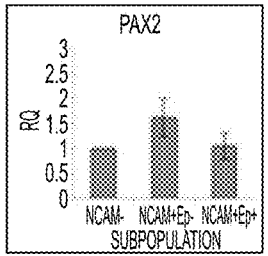
Figure 9L:
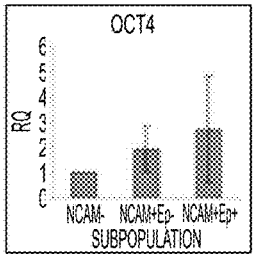
Figure 9Q:
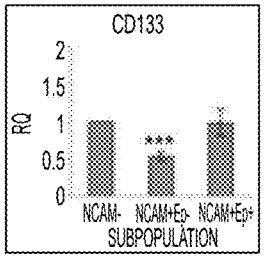
Figure 10A:
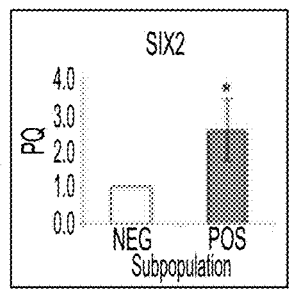
FIGS. 10A-G are graphs illustrating gene expression analysis in sorted PSA-NCAM subpopulations. Quantitative reverse transcription-polymerase chain reaction (qRT-PCR) analysis of (FIGS. 10A-E) renal stem/progenitor genes (Six2, Cited1, Sall1, Wt1 and Pax2), (FIGS. 10 F-G) vimentin and E-cadherin genes expression in PSA-NCAM magnetically separated cells from HFK (15-19 weeks of gestation). Normalization was performed against control HPRT expression and RQ calculated relative to the PSA-NCAM$^-$ fraction. Data were calculated as average±SD of at least 3 independent samples. ***P<0.001, *P<0.05 versus PSA-NCAM$^-$. Sall1 expression in NCAM$^+$EpCAM$^+$ cells was near significance (p<0.059).
Figure 10B:
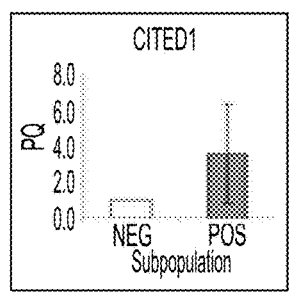
Figure 10C:
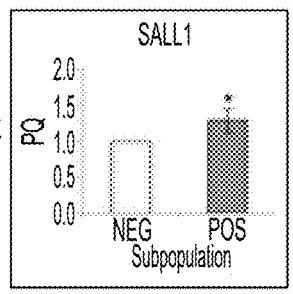
Figure 10D:
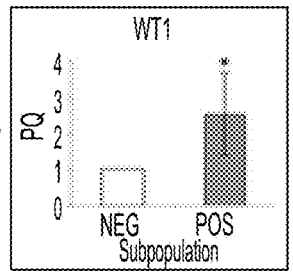
Figure 10E:
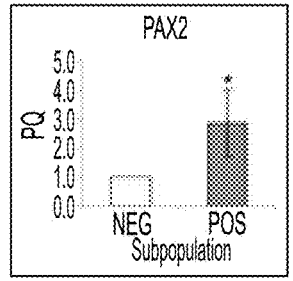
Figure 10F:
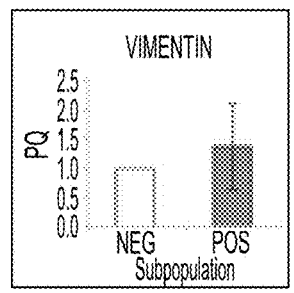
Figure 10G:
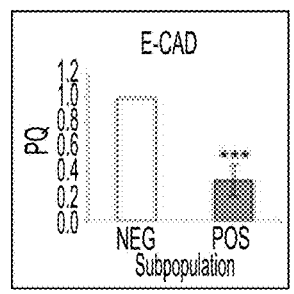

Although a heterogeneous cell population, NCAM+EpCAM− cells highly overexpressed (>five fold) most MM stem/progenitor genes in five separate HFK (FIGS. 9A-E), levels of which were already reduced in the NCAM+EpCAM+ cell fraction (presumably more differentiated), but still higher (Wt1, Sall1) in comparison with the NCAM− cell fraction, indicating a hierarchy for enrichment for the renal 'progenitor' genes. Considerably lower E-cad levels were observed for the NCAM+EpCAM− and NCAM+EpCAM+ cell fractions, while NCAM+EpCAM− also significantly overexpressed vimentin (FIGS. 9F-G). In addition, while there was a tendency for elevation of the 'stemness genes' in the NCAM+ fractions, only B-catenin achieved significance in NCAM+EpCAM− cells (FIGS. 9H-L), most likely due to large variations across human samples. Finally, analysis of surface marker expression in the sorted subpopulations showed elevated FZD7, ACVRIIB and NTRK2 in the NCAM+ fractions (both FZD7 and NTRK2 genes significantly overexpressed in the NCAM+EpCAM− fractions) as opposed to CD24 and especially CD133 (FIGS. 9M-Q). Similar results were found when analyzing expression in sorted PSA-NCAM+ cells by comparison to the negative fraction. PSA-NCAM (see before) showed significant enrichment for Six2, Sall1, Wt1 and Pax2 (FIGS. 10A-E and 10 H-I, J and M)) as well as reduced levels of E-cadherin (FIGS. 10E-G and 10L), all indicative of a stem/progenitor origin. Thus, HFK cells retain aspects of regional identity as determined by marker immunostaining.

Example 3

HFK Cell Sub Populations Sorted According to Specific Markers Show Enhanced 'Stemness' Function Following verification of the renal 'stemness' gene profile in human renal stem/progenitors sorted according to specific markers, the present inventors analyzed these fractions for clonogenic ability, an important feature of stem/progenitor cells.

Materials and Methods

Limiting dilution assay was performed on HFK cells sorted according to NCAM and PSA-NCAM. Both positive and negative fractions were plated in 96-well micro well plates at 0.3, 1, 3 and 5 cells per well dilution. The number of colonized wells was recorded after 3-4 weeks.

In addition HFK cells were sorted according to ALDH expression and the clonogenic ability was tested in serum containing medium and serum free medium.

Flow Cytometry:

Flow cytometry was performed as described in Example 1, herein above. Detection of cells with high ALDH1 enzymatic activity was performed using the ALDEFLUOR kit (StemCell Technologies, Durham, N.C., USA).

Results

Figure 11A:
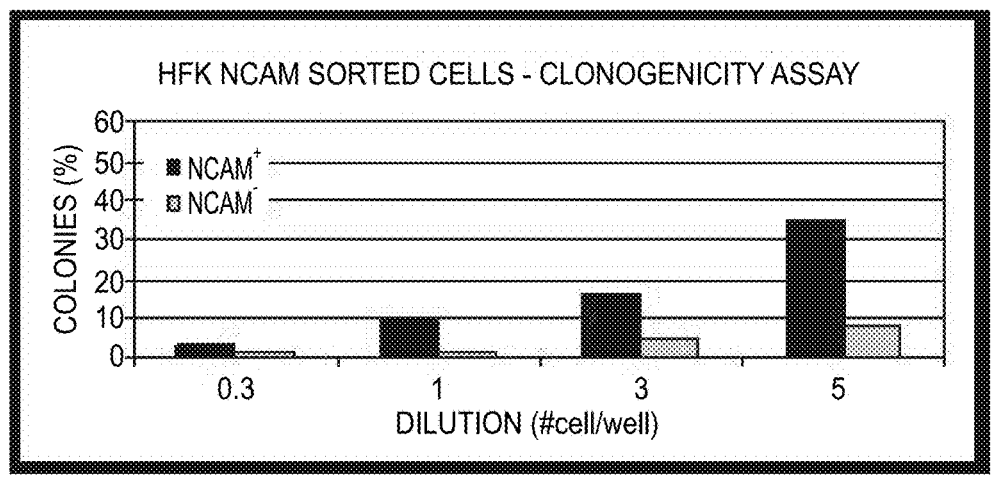
FIGS. 11A-B are graphs illustrating assessment of clonogenic capacities of isolated HFK cells sorted according to NCAM and PSA-NCAM surface markers. Data of sorted (11A) NCAM+ and (11B) PSA-NCAM+ cells show their high clonogenic potential in all concentrations.
Figure 11B:
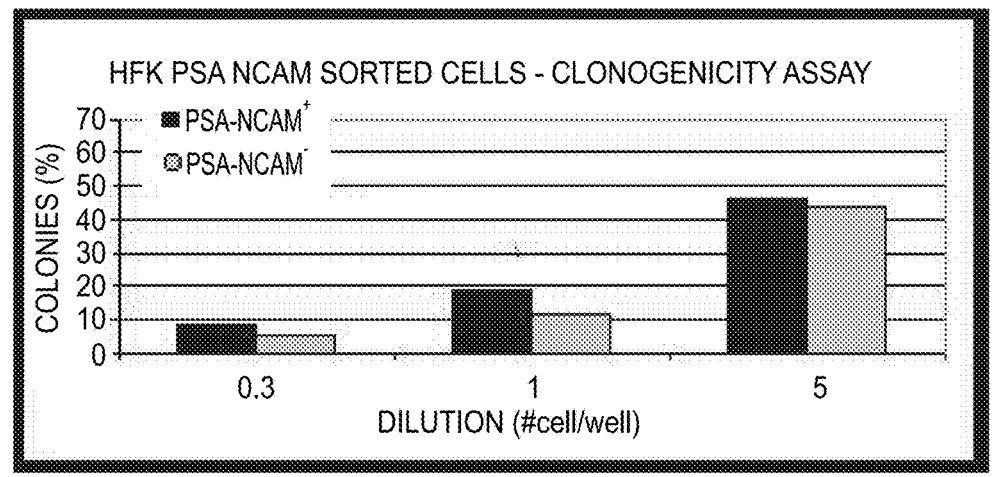
Figure 12A:
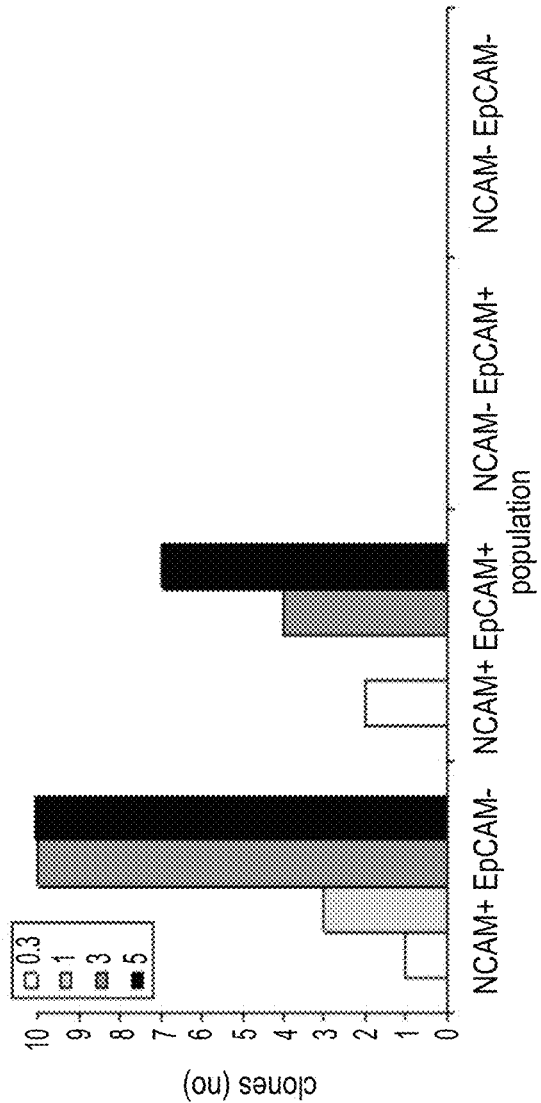
FIGS. 12A-B are graphs and photographs illustrating the results of the limiting dilution assay which was performed on HFK cells sorted according to NCAM+EpCAM−, NCAM+EpCAM+ and NCAM−EpCAM+ and NCAM−EpCAM−. All cell fractions were plated in 96-well micro well plates at 0.3, 1, 3 and 5 cells per well dilution. The number of colonized wells was recorded after 3-4 weeks. NCAM+EpCAM− cells show highest clonogenic potential and to a lesser extent NCAM+EpCAM+ fraction compared to NCAM−EpCAM+ and NCAM−EpCAM− cells which formed no clones.
Figure 12B:
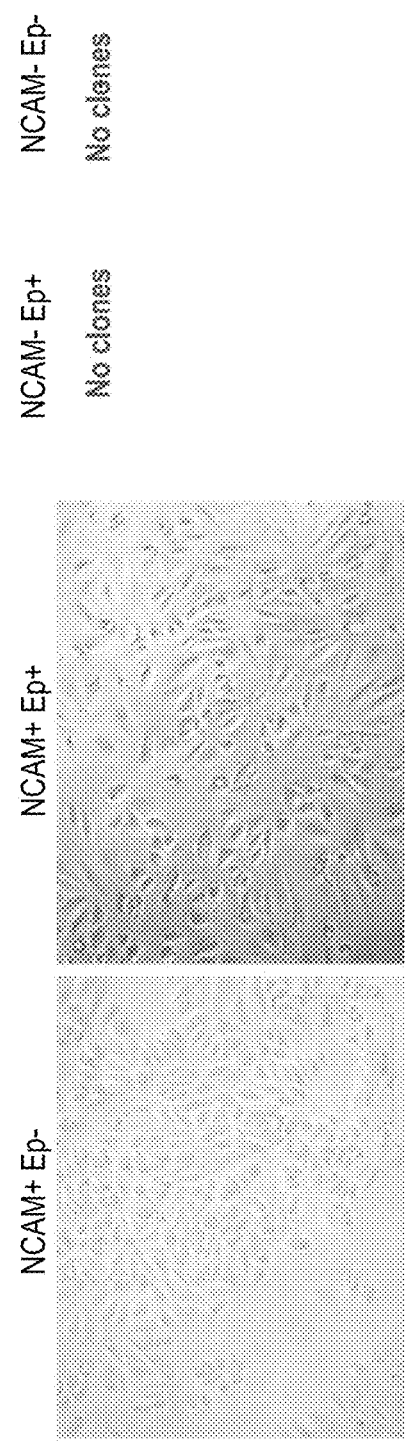

Enhanced clonogenic capacity was found for sorted NCAM+ and PSA-NCAM+ cells (FIGS. 11A-B). In addition it was found that when culturing sorted cells in serum free media, a media that preserves epithelial kidney stem/progenitor cells the entire clonogenic capabilities of HFK cells are within the NCAM+ fraction, both NCAM+EpCAM− and NCAM+EpCAM+ (the first has an advantage over the second) stem/progenitor fractions but not in differentiated NCAM− fraction (both EpCAM+ or EpCAM−) (FIGS. 12A-B).

Enhanced clonogenic capacity was found for sorted ALDH+/bright cells (FIG. 13A) compared to ALDH− cells.

Furthermore ALDH+/bright sorted cells showed enhanced expression of renal progenitor genes compared with ALDH$^{neg}$ cells as measured by qRT PCR (FIGS. 13B-E).

Example 4

HFK Cell Sub Populations Cultured in Serum Free Medium Preserves Expression of Stem-Cell Associated Markers Materials and Methods Culturing of HFK Cells:

Cells were grown in DMEM:F12, a 1:1 mixture of Ham's F12 and high-glucose Dulbecco's modified Eagle medium supplemented with 1% non essential Amino acids, 1% of sodium pyruvate (all from Invitrogen, Carlsbad, Calif., USA), 1% N2 supplement 100×, 0.4% B27 supplement (both from Gibco, Carlsbad, Calif., USA), 0.2% Lipid mixture, 1% growth factor mixture containing 2% glucose 30%, 200 mg transferring, 50 mg insulin, 0.1% sodium selanite 0.3 mM, 0.01% progesterone 2 Mm and 19.33 mg putrescine (all from Sigma-Aldrich, St Louis, Mo., USA), 4 µg/ml heparin, supplemented with 10 ng/ml FGF, 20 ng/ml EGF (R&D Systems, Inc, Minneapolis, USA). For passage, cells cultured in serum-free media were dissociated with Cell dissociation solution (Sigma-Aldrich) without trypsin.

Experiments were preformed on low passages qRT-PCR Analysis:

RT-PCR analysis was performed as described in Example 2, herein above.

Results

Figure 14A:
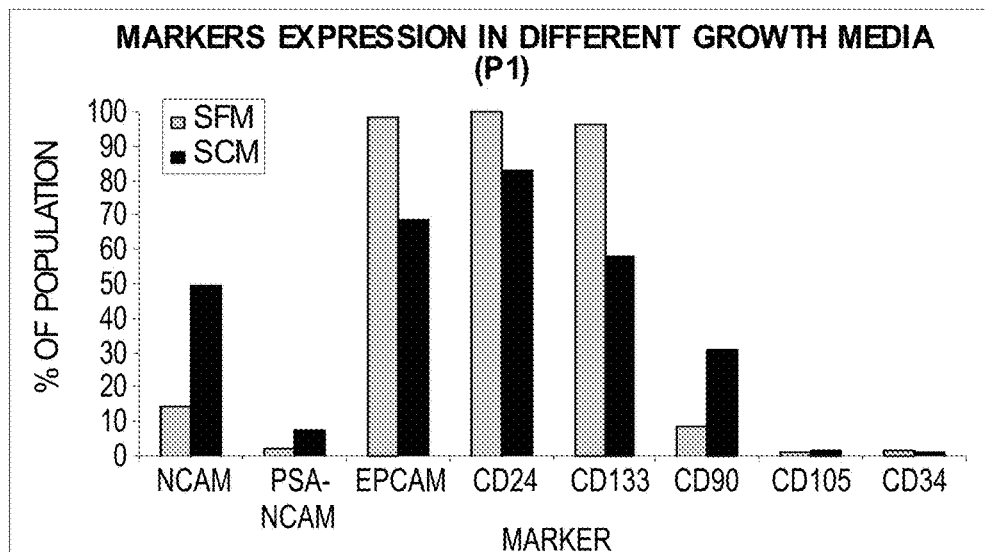
FIGS. 14A-B are bar graphs comparing the effect of serum free medium and serum containing medium on surface marker expression levels in human fetal kidney cells.
Figure 14B:
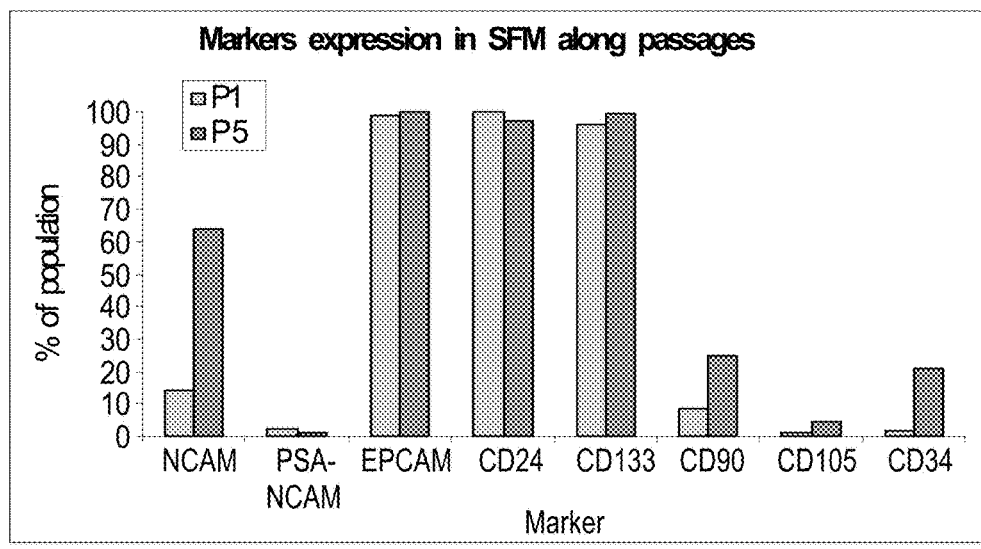

HFK cells cultured in serum free medium showed different expression levels surface markers compared to HFK cells cultured in serum containing medium as illustrated in FIG. 14A. FIG. 14B illustrates that high expression of particular markers (namely CD24, CD133 and EPCAM) is preserved following 5 passages in serum free medium; whereas expression of NCAM is increased following 5 passages.

In addition, HFK cells cultured in serum free medium showed elevated expression levels of nephric progenitor genes (FIGS. 15A-C), compared to HFK cells. E-cadherein expression was more rapidly lost in serum containing medium than serum free medium (FIG. 15D) and FoxD1 (indicative of stromal cells) expression was shown to be elevated in serum containing medium compared to serum free medium (FIG. 15E).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Weissman, I. L. Translating stem and progenitor cell biology to the clinic: barriers and opportunities. Science 287, 1442-1446 (2000).
2. Xu, A. S. L. et al. Principles of Tissue Engineering, eds. (Lanza, R. P. Langer, R. Chick, W. L., Academic, San Diego; 2000).
3. Dekel, B. & Reisner, Y. Applications of tissue engineering for the treatment of renal and uro-genital disease (chapter eds.), Vol. 208. (Battler A., Leor J, Springer-Verlag London; 2006).
4. Cho, E. A. & Dressler, G. R. In The Kidney: From Normal Development to Congenital Disease, Edn. P. Vize, A. S. Woolf and J. B. L. Bard. (San Diego: Academic Press, San Diego; 2003).
5. Woolf, A. S. The life of the human kidney before birth: its secrets unfold. Pediatr Res 49, 8-10 (2001).
6. Rosenblum, N. D. Developmental biology of the human kidney. Semin Fetal Neonatal Med 13, 125-132 (2008).
7. Self, M. et al. Six2 is required for suppression of nephrogenesis and progenitor renewal in the developing kidney. Embo J 25, 5214-5228 (2006).
8. Boyle, S. et al. Fate mapping using Cited1-CreERT2 mice demonstrates that the cap mesenchyme contains self-renewing progenitor cells and gives rise exclusively to nephronic epithelia. Dev Biol 313, 234-245 (2008).
9. Kobayashi, A. et al. Six2 defines and regulates a multipotent self-renewing nephron progenitor population throughout mammalian kidney development. Cell Stem Cell 3, 169-181 (2008).
10. Dekel, B. et al. Engraftment of human kidney tissue in rat radiation chimera: II. Human fetal kidneys display reduced immunogenicity to adoptively transferred human peripheral blood mononuclear cells and exhibit rapid growth and development. Transplantation 64, 1550-1558 (1997).
11. Dekel, B. et al. Engraftment and differentiation of human metanephroi into functional mature nephrons after transplantation into mice is accompanied by a profile of gene expression similar to normal human kidney development. J Am Soc Nephrol 13, 977-990 (2002).
12. Dekel, B. et al. Human and porcine early kidney precursors as a new source for transplantation. Nat Med 9, 53-60 (2003).
13. Kim, S. S. et al. Kidney tissue reconstruction by fetal kidney cell transplantation: effect of gestation stage of fetal kidney cells. Stem Cells 25, 1393-1401 (2007).
14. Kim, S. S. et al Improvement of kidney failure with fetal kidney precursor cell transplantation. Transplantation 83, 1249-1258 (2007).
15. Brodbeck, S. & Englert, C. Genetic determination of nephrogenesis: the Pax/Eya/Six gene network. Pediatr Nephrol 19, 249-255 (2004).
16. Dekel, B. et al. Multiple imprinted and stemness genes provide a link between normal and tumor progenitor cells of the developing human kidney. Cancer Res 66, 6040-6049 (2006).
17. Rivera, M. N. & Haber, D. A. Wilms' tumour: connecting tumorigenesis and organ development in the kidney. Nat Rev Cancer 5, 699-712 (2005).
18. Metsuyanim, S. et al. Accumulation of malignant renal stem cells is associated with epigenetic changes in normal renal progenitor genes. Stem Cells 26, 1808-1817 (2008).
19. Kreidberg, J. A. et al. WT-1 is required for early kidney development. Cell 74, 679-691 (1993).
20. Nishinakamura, R. Kidney development conserved over species: essential roles of Sal11. Semin Cell Dev Biol 14, 241-247 (2003).
21. da Silva Meirelles, L., Chagastelles, P. C. & Nardi, N. B. Mesenchymal stem cells reside in virtually all post-natal organs and tissues. J Cell Sci 119, 2204-2213 (2006).
22. Trzpis, M. et al. EpCAM homologues exhibit epithelial-specific but different expression patterns in the kidney. Transgenic Res 17, 229-238 (2008).
23. Trzpis, M. et al. Spatial and temporal expression patterns of the epithelial cell adhesion molecule (EpCAM/EGP-2) in developing and adult kidneys. Nephron Exp Nephrol 107, e119-131 (2007).
24. Klein, G., Langegger, M., Goridis, C. & Ekblom, P. Neural cell adhesion molecules during embryonic induction and development of the kidney. Development 102, 749-761 (1988).
25. Bard, J. B., Gordon, A., Sharp, L. & Sellers, W. I. Early nephron formation in the developing mouse kidney. J Anat 199, 385-392 (2001).
26. Roth, J., Blaha, I., Bitter-Suermann, D. & Heitz, P. U. Blastemal cells of nephroblastomatosis complex share an onco-developmental antigen with embryonic kidney and Wilms' tumor. An immunohistochemical study on polysialic acid distribution. Am J Pathol 133, 596-608 (1988).
27. Schmidt-Ott, K. M. & Barasch, J. WNT/beta-catenin signaling in nephron progenitors and their epithelial progeny. Kidney Int 74, 1004-1008 (2008).
28. Oh, S. P. & Li, E. The signaling pathway mediated by the type IIB activin receptor controls axial patterning and lateral asymmetry in the mouse. Genes Dev 11, 1812-1826 (1997).
29. Esquela, A. F. & Lee, S. J. Regulation of metanephric kidney development by growth/differentiation factor 11. Dev Biol 257, 356-370 (2003).
30. Durbeej, M., Soderstrom, S., Ebendal, T., Birchmeier, C. & Ekblom, P. Differential expression of neurotrophin receptors during renal development. Development 119, 977-989 (1993).
31. Dekel, B. et al. Transplantation of human hematopoietic stem cells into ischemic and growing kidneys suggests a role in vasculogenesis but not tubulogenesis. Stem Cells 24, 1185-1193 (2006).
32. Dominici, M. et al. Minimal criteria for defining multipotent mesenchymal stromal cells. The International Society for Cellular Therapy position statement. Cytotherapy 8, 315-317 (2006).
33. Challen, G. A. et al. Identifying the molecular phenotype of renal progenitor cells. J Am Soc Nephrol 15, 2344-2357 (2004).
34. Lazzeri, E. et al. Regenerative potential of embryonic renal multipotent progenitors in acute renal failure. J Am Soc Nephrol 18, 3128-3138 (2007).
35. Shmelkov, S. V. et al. CD133 expression is not restricted to stem cells, and both CD133+ and CD133-metastatic colon cancer cells initiate tumors. J Clin Invest 118, 2111-2120 (2008).
36. Salven, P., Mustjoki, S., Alitalo, R., Alitalo, K. & Rafii, S. VEGFR-3 and CD133 identify a population of CD34+ lymphatic/vascular endothelial precursor cells. Blood 101, 168-172 (2003).

37. Uchida, N. et al. Direct isolation of human central nervous system stem cells. Proc Natl Acad Sci USA 97, 14720-14725 (2000).
38. Sugiyama, T., Rodriguez, R. T., McLean, G. W. & Kim, S. K. Conserved markers of fetal pancreatic epithelium permit prospective isolation of islet progenitor cells by FACS. Proc Natl Acad Sci USA 104, 175-180 (2007).
39. Sagrinati, C. et al. Isolation and characterization of multipotent progenitor cells from the Bowman's capsule of adult human kidneys. J Am Soc Nephrol 17, 2443-2456 (2006).
40. Weigmann, A., Corbeil, D., Hellwig, A. & Huttner, W. B. Prominin, a novel microvilli-specific polytopic membrane protein of the apical surface of epithelial cells, is targeted to plasmalemmal protrusions of non-epithelial cells. Proc Natl Acad Sci USA 94, 12425-12430 (1997).
41. Pode-Shakked, N. et al. Developmental tumorigenesis: NCAM as a putative marker for the malignant renal stem/progenitor cell population. J Cell Mol Med (2008 November in print).
42. Loo, D., Beltejar, C., Hooley, J. & Xu, X. Primary and multipassage culture of human fetal kidney epithelial progenitor cells. Methods Cell Biol 86, 241-255 (2008).

What is claimed is:

1. A method of treating a renal damage in a subject in need thereof comprising administering to the subject a therapeutically effective amount of renal cells comprising at least 50% cells having a NCAM+ signature, thereby treating the renal damage in the subject.

2. The method of claim 1, wherein said administering is to a damaged kidney of the subject.

3. The method of claim 1, wherein said renal cells comprising at least 50% cells having a NCAM+ signature comprise a NCAM+/EpCAM+ signature.

4. The method of claim 1, wherein said renal cells comprising at least 50% cells having a NCAM+ signature comprise a NCAM+/CD133+ signature.

5. The method of claim 1, wherein said renal cells comprising at least 50% cells having a NCAM+ signature comprise a NCAM+/CD24+ signature.

6. The method of claim 1, further comprising enriching for said renal cells comprising at least 50% cells having a NCAM+ signature by culturing fetal renal cells of a fetal renal tissue in a culture medium devoid of serum prior to said administering.

7. The method of claim 1, wherein said renal cells are seeded on a scaffold.

8. The method of claim 1, wherein said renal cells comprise at least 60% cells having a NCAM+ signature.

9. The method of claim 1, wherein said renal cells comprise at least 70% cells having a NCAM+ signature.

* * * * *